(12) United States Patent
Miyazaki

(10) Patent No.: US 11,439,314 B2
(45) Date of Patent: Sep. 13, 2022

(54) IMAGE PROCESSING APPARATUS, MAGNETIC RESONANCE IMAGING APPARATUS, AND IMAGE PROCESSING METHOD

(71) Applicant: CANON MEDICAL SYSTEMS CORPORATION, Otawara (JP)

(72) Inventor: Mitsue Miyazaki, Vernon Hills, IL (US)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 471 days.

(21) Appl. No.: 16/561,799

(22) Filed: Sep. 5, 2019

(65) Prior Publication Data

US 2021/0068698 A1 Mar. 11, 2021

(51) Int. Cl.
*A61B 5/055* (2006.01)
*G01R 33/56* (2006.01)
*G01R 33/483* (2006.01)
*G01R 33/54* (2006.01)
*G01R 33/48* (2006.01)
*G01R 33/561* (2006.01)

(52) U.S. Cl.
CPC .......... *A61B 5/055* (2013.01); *G01R 33/4835* (2013.01); *G01R 33/5605* (2013.01); *G01R 33/4818* (2013.01); *G01R 33/543* (2013.01); *G01R 33/5608* (2013.01); *G01R 33/5615* (2013.01); *G06T 2207/10088* (2013.01)

(58) Field of Classification Search
CPC .. A61B 5/055; A61B 5/4064; G01R 33/4818; G01R 33/4835; G01R 33/543; G01R 33/5605; G01R 33/5608; G01R 33/5615; G01R 33/50; G01R 33/56; G01R 33/5602; G06T 2207/30016; G06T 7/11
See application file for complete search history.

(56) References Cited

U.S. PATENT DOCUMENTS

| | | | | |
|---|---|---|---|---|
| 6,076,004 | A * | 6/2000 | Kanayama | ............. A61B 5/055 324/309 |
| 9,766,313 | B2 | 9/2017 | Eggers et al. | |
| 2012/0184843 | A1* | 7/2012 | Kao | ..................... A61B 5/4064 600/419 |
| 2013/0194265 | A1* | 8/2013 | Rehwald | ................. G06T 15/08 345/419 |
| 2014/0062473 | A1 | 3/2014 | Miyazaki et al. | |

(Continued)

FOREIGN PATENT DOCUMENTS

JP 2015-144825 A 8/2015
JP 2017-196529 A 11/2017

OTHER PUBLICATIONS

Miyazaki, M. et al. "Z-Spectrum Analysis Provides Proton Environment Data (ZAPPED): A New Two-Pool Technique for Human Gray and White Matter", PLOS ONE, Mar. 13, 2015, 12 pages.

*Primary Examiner* — Steven L Yeninas
(74) *Attorney, Agent, or Firm* — Oblon, McClelland, Maier & Neustadt, L.L.P.

(57) ABSTRACT

An image processing apparatus according to an embodiment includes processing circuitry. The processing circuitry generates an image by performing an analysis based on a Z-spectrum generated based on data obtained by executing a pulse sequence including application of a Magnetization Transfer (MT) pulse and causes a display to display the generated image by dividing the image into a plurality of segments.

14 Claims, 18 Drawing Sheets

(56) References Cited

U.S. PATENT DOCUMENTS

| | | |
|---|---|---|
| 2014/0062476 A1 | 3/2014 | Miyazaki et al. |
| 2014/0361776 A1 | 12/2014 | Miyazaki et al. |
| 2015/0219735 A1 | 8/2015 | Miyazaki et al. |
| 2015/0297190 A1* | 10/2015 | Selker .................. A61B 8/0875 600/440 |
| 2020/0284864 A1* | 9/2020 | Damen ................ G01R 33/465 |

* cited by examiner

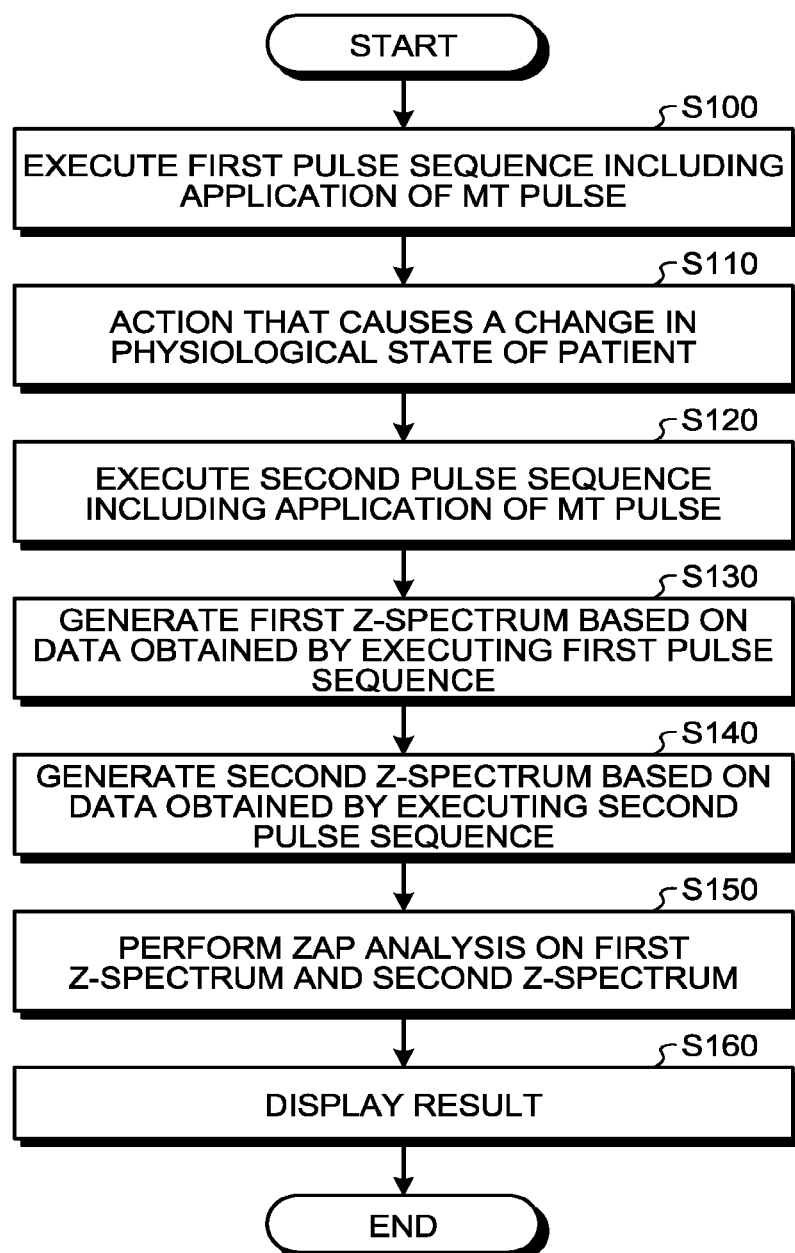

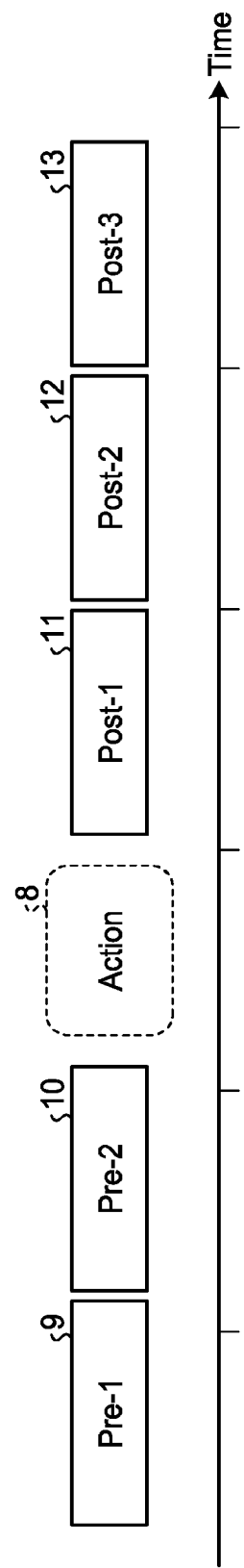

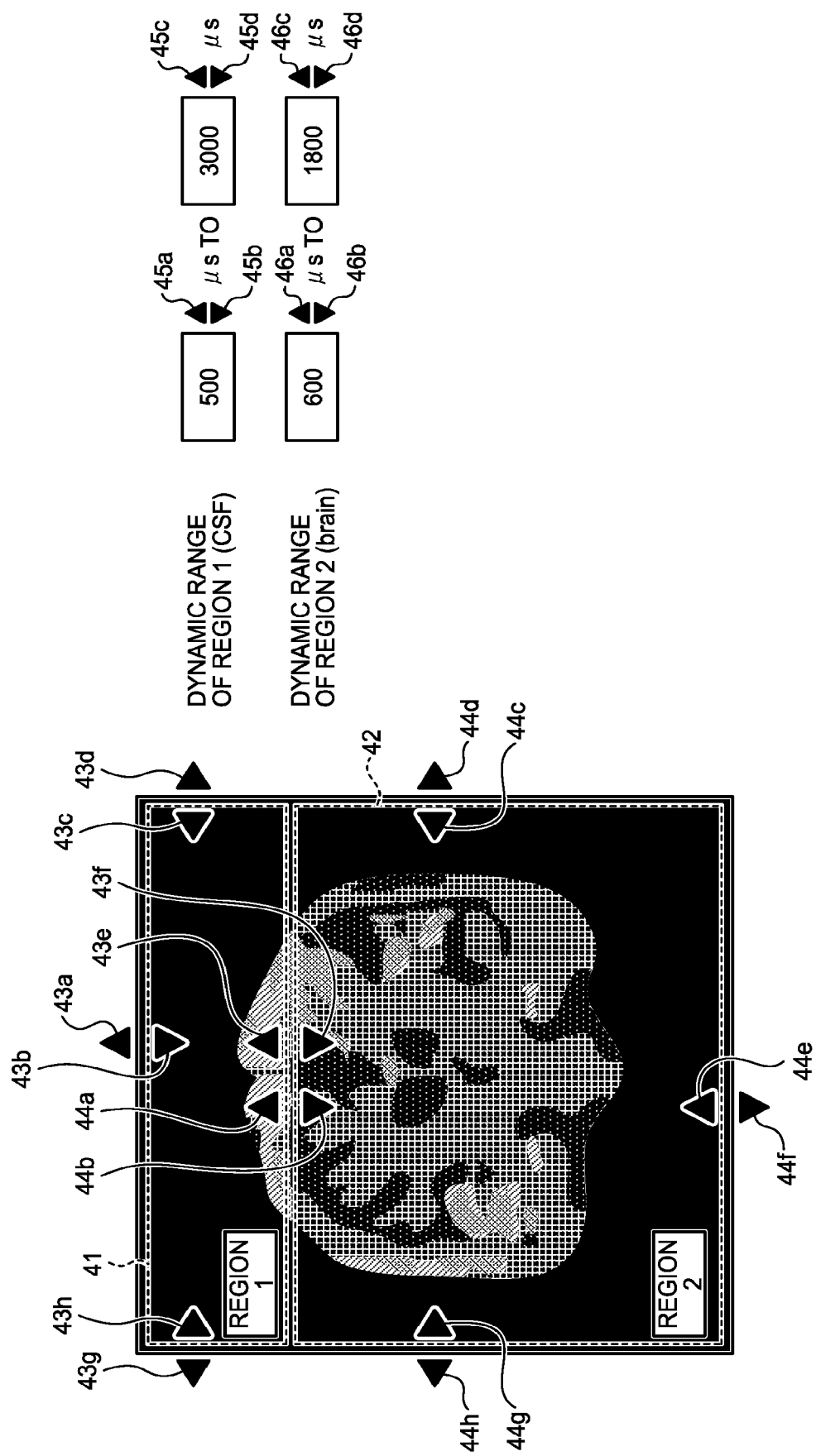

FIG.13

| EXAMPLES | | | ZAP VALUES IN EACH SEGMENT OF CSF | | | | DIFFERENCE BETWEEN PRE-ACTION AND POST-ACTION | | | |
|---|---|---|---|---|---|---|---|---|---|---|
| | | | $T_{2,f}\,(\mu s)$ | $T_{2,r}\,(\mu s)$ | Ff% | Fr% | $T_{2,f}\,(\mu s)$ | $T_{2,r}\,(\mu s)$ | Ff% | Fr% |
| Coronal | | 12:00 - 1:30 O'CLOCK | 1700 | 10 | 76 | 24 | -15 | -5 | +3 | -6 |
| Sagittal Center | | 1:30 - 3:00 O'CLOCK | 2950 | 8 | 82 | 18 | +9 | +6 | -5 | +9 |
| | | 3:00 - 4:30 O'CLOCK | 2200 | 10 | 76 | 24 | +3 | -6 | -15 | +9 |
| | | 4:30 - 6:00 O'CLOCK | 2000 | 10 | 75 | 25 | -5 | +9 | +9 | -5 |
| | | 6:00 - 7:30 O'CLOCK | 2050 | 8 | 80 | 20 | +6 | +9 | +3 | +6 |
| | | 7:30 - 9:00 O'CLOCK | 2240 | 10 | 80 | 20 | -6 | +3 | -5 | -6 |
| | | 9:00 - 10:30 O'CLOCK | 3050 | 9 | 82 | 18 | +9 | -5 | +6 | +9 |
| | | 10:30 - 12:00 O'CLOCK | 1750 | 10 | 75 | 25 | +14 | +6 | +6 | +12 |
| Axial | | 12:00 - 1:30 O'CLOCK | 1800 | 8 | 88 | 22 | -11 | -5 | +3 | -6 |
| | | 1:30 - 3:00 O'CLOCK | 3000 | 8 | 82 | 18 | +9 | +6 | -5 | +4 |
| | | 3:00 - 4:30 O'CLOCK | 2250 | 9 | 76 | 24 | +3 | -6 | -10 | +9 |
| | | 4:30 - 6:00 O'CLOCK | 1950 | 7 | 74 | 26 | -5 | -7 | +8 | -5 |
| | | 6:00 - 7:30 O'CLOCK | 2000 | 8 | 81 | 19 | +6 | +9 | +3 | +6 |
| | | 7:30 - 9:00 O'CLOCK | 2200 | 8 | 82 | 18 | -7 | 0 | -5 | -6 |
| | | 9:00 - 10:30 O'CLOCK | 3000 | 9 | 80 | 20 | +8 | -5 | +6 | +9 |
| | | 10:30 - 12:00 O'CLOCK | 1800 | 7 | 74 | 26 | +9 | +6 | +3 | +11 |

IMAGE PROCESSING APPARATUS, MAGNETIC RESONANCE IMAGING APPARATUS, AND IMAGE PROCESSING METHOD

FIELD

Embodiments described herein relate generally to an image processing apparatus, a magnetic resonance imaging apparatus, and an image processing method.

BACKGROUND

Among magnetic resonance imaging schemes, imaging schemes using a Magnetization Transfer Contrast (MTC) effect are drawing attention. With the MTC effect, it is possible to observe an exchange of magnetism between free water protons and restricted protons in a polymer. It is therefore possible to render a composition of a tissue in an image.

As an example of the imaging schemes using the MTC effect, a so-called Chemical Exchange Saturation Transfer (CEST) method is known by which specific exchangeable protons are selectively saturated, so as to observe a free water signal after the saturation.

The CEST method, however, places a focus on a signal region related to the frequency region of offset frequencies that are usually in the range of approximately ±1,000 Hz compared to the frequency of the free water signal. Accordingly, no focus is placed on signal components having a width larger than the offset frequencies in the range of approximately ±1,000 Hz.

BRIEF DESCRIPTION OF THE DRAWINGS

FIG. 2 is a flowchart illustrating a processing procedure performed by a magnetic resonance imaging apparatus according to a first embodiment;

FIG. 4 is a drawing illustrating a process performed by the magnetic resonance imaging apparatus according to the first embodiment;

FIG. 9 is a drawing illustrating an example of a Graphical User Interface (GUI) related to the magnetic resonance imaging apparatus according to the second embodiment;

FIG. 13 is a drawing for explaining a process performed by the magnetic resonance imaging apparatus according to the second embodiment.

DETAILED DESCRIPTION

Figure 1:
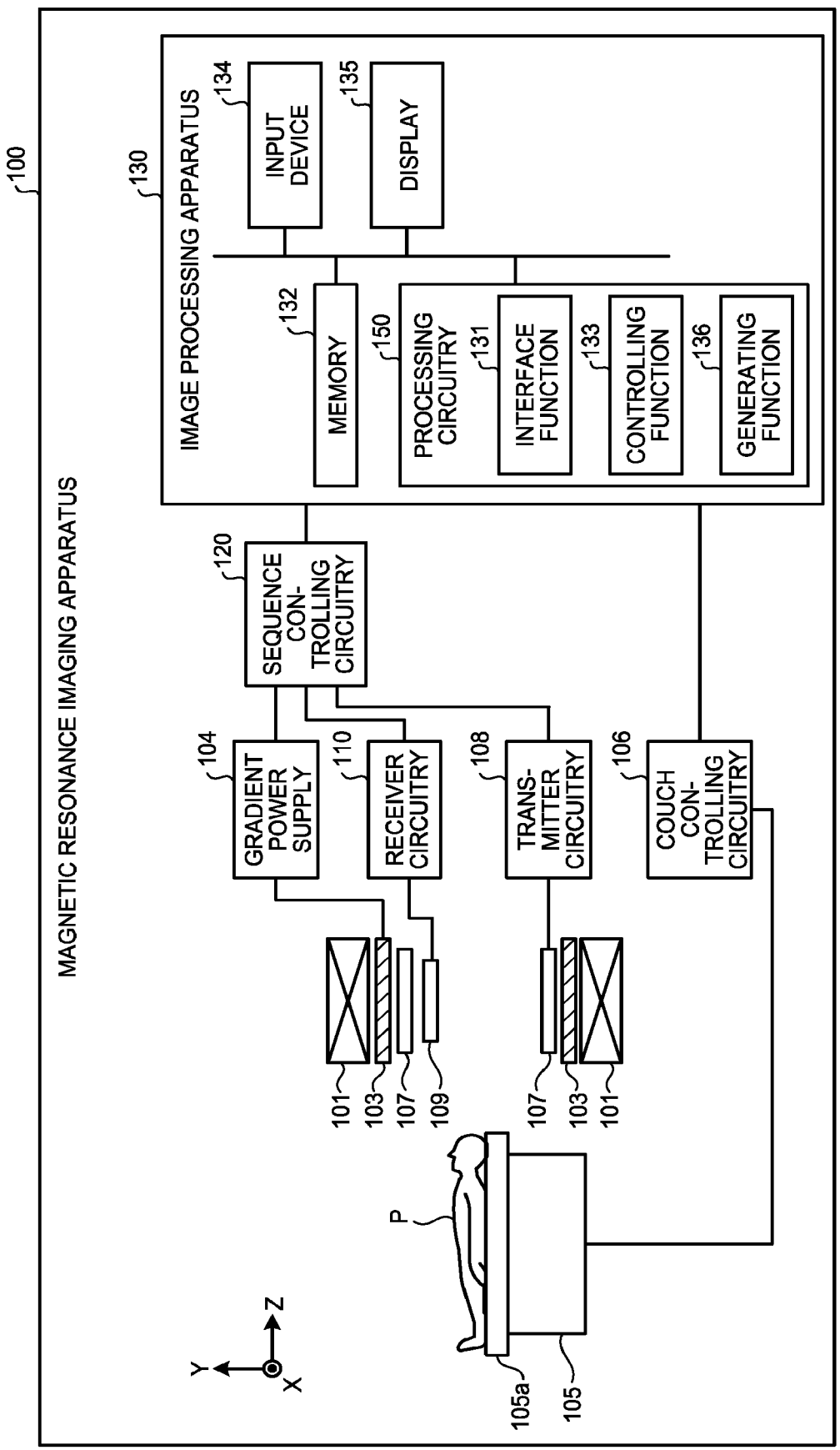
FIG. 1 is a diagram illustrating a magnetic resonance imaging apparatus according to an embodiment.
Figure 3A:
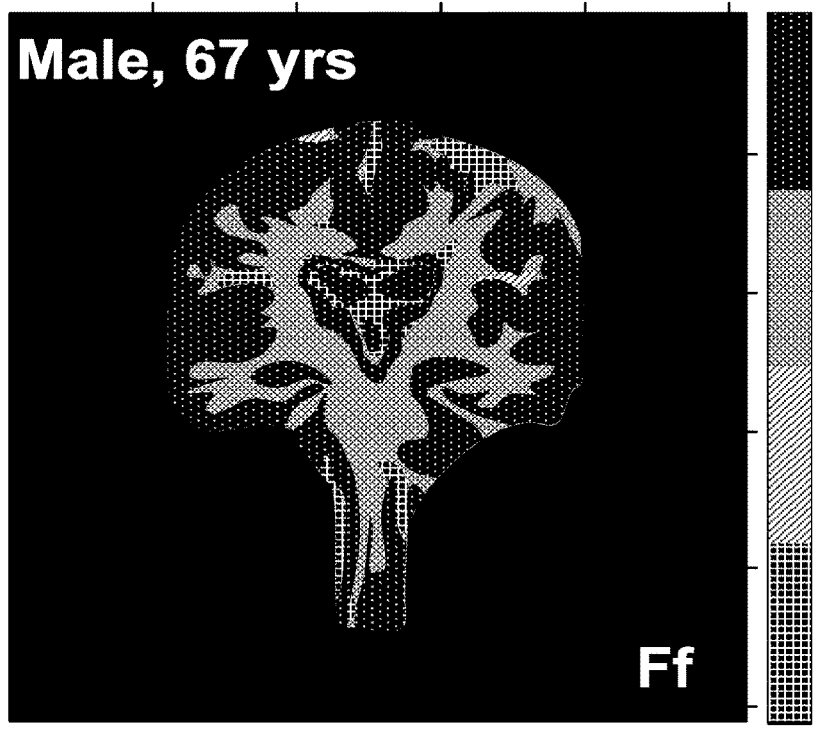
FIGS. 3A, 3B, 3C, and 3D are drawings illustrating examples of images obtained by the magnetic resonance imaging apparatus according to the first embodiment.
Figure 3B:
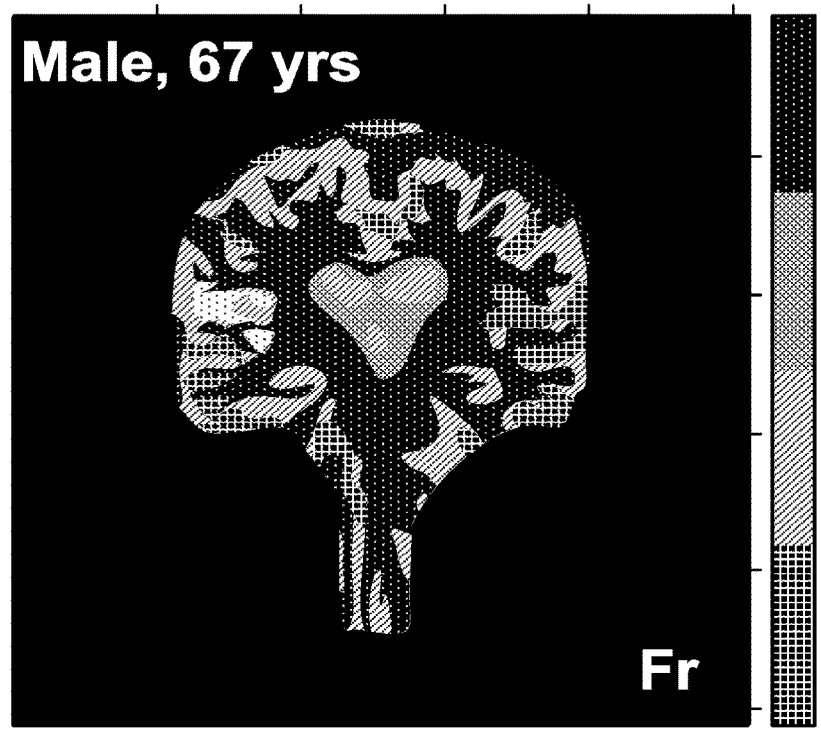
Figure 3C:
Figure 3D:

An image processing apparatus according to an embodiment includes processing circuitry. The processing circuitry generates an image by performing an analysis based on a Z-spectrum generated based on data obtained by executing a pulse sequence including application of a Magnetization Transfer (MT) pulse and causes a display to display the generated image by dividing the image into a plurality of segments.

Exemplary embodiments of the present disclosure will be explained below, with reference to the accompanying drawings. In the following sections, some of the constituent elements that are the same as each other will be referred to by using the same reference characters, and the duplicate explanations thereof will be omitted.

First Embodiment

FIG. 1 is a block diagram illustrating a magnetic resonance imaging apparatus 100 according to a first embodiment. As illustrated in FIG. 1, the magnetic resonance imaging apparatus 100 includes a static magnetic field magnet 101, a static magnetic field power supply (not illustrated), a gradient coil 103, a gradient power supply 104, a couch 105, couch controlling circuitry 106, a transmitter coil 107, transmitter circuitry 108, a receiver coil 109, receiver circuitry 110, sequence controlling circuitry 120 (a sequence controlling unit), and an image processing apparatus 130. An examined subject (hereinafter, "patient") P (e.g., a human body) is not included in the magnetic resonance imaging apparatus 100. Further, the configuration illustrated in FIG. 1 is merely an example. For example, any of the functional units in the sequence controlling circuitry 120 and the image processing apparatus 130 may be integrated together or configured separately as appropriate.

The static magnetic field magnet 101 is a magnet formed to have a hollow and circular cylindrical shape and is configured to generate a static magnetic field in the space inside thereof. For example, the static magnetic field magnet 101 is a superconductive magnet or the like and gets magnetically excited by receiving supply of an electric current from the static magnetic field power supply. The static magnetic power supply is configured to supply the electric current to the static magnetic field magnet 101. Alternatively, the static magnetic field magnet 101 may be a permanent magnet. In that situation, the magnetic resonance imaging apparatus 100 does not have to be provided with a static magnetic field power supply. Further, the static magnetic field power supply may be provided separately from the magnetic resonance imaging apparatus 100.

The gradient coil 103 is a coil formed to have a hollow and circular cylindrical shape and is arranged on the inside of the static magnetic field magnet 101. The gradient coil 103 is formed by combining together three coils corresponding to X-, Y-, and Z-axes that are orthogonal to one another.

The three coils are configured to individually receive supply of an electric current from the gradient power supply 104 and to generate gradient magnetic fields of which the magnetic field intensities vary along the X-, Y-, and Z-axes. The gradient magnetic fields generated along the X-, Y-, and Z-axes by the gradient coil 103 are, for example, a slice gradient magnetic field Gs, a phase-encoding gradient magnetic field Ge, and a read-out gradient magnetic field Gr. The gradient power supply 104 is configured to supply the electric current to the gradient coil 103.

The couch 105 includes a couchtop 105a on which the patient P is placed. Under control of the couch controlling circuitry 106, the couchtop 105a is inserted to the inside of the hollow space (an image taking opening) of the gradient coil 103 while the patient P is placed thereon. Normally, the couch 105 is installed in such a manner that the longitudinal direction thereof extends parallel to the central axis of the static magnetic field magnet 101. Under control of the image processing apparatus 130, the couch controlling circuitry 106 is configured to drive the couch 105 so as to move the couchtop 105a in longitudinal directions and up-and-down directions.

The transmitter coil 107 is arranged on the inside of the gradient coil 103 and is configured to generate a radio frequency magnetic field by receiving supply of a Radio Frequency (RF) pulse from the transmitter circuitry 108. The transmitter circuitry 108 is configured to supply the transmitter coil 107 with the RF pulse corresponding to a Larmor frequency determined by the type of a target atom and the intensity of the magnetic field.

The receiver coil 109 is arranged on the inside of the gradient coil 103 and is configured to receive a magnetic resonance signal (which hereinafter may be referred to as "MR signal" as necessary) emitted from the patient P due to the influence of the radio frequency magnetic field. When having received the magnetic resonance signal, the receiver coil 109 is configured to output the received magnetic resonance signal to the receiver circuitry 110.

The transmitter coil 107 and the receiver coil 109 described above are merely examples. It is possible to use one or a combination of two or more, from among the following: a coil having only a transmitting function; a coil having only a receiving function; and a coil having transmitting and receiving functions.

The receiver circuitry 110 is configured to detect the magnetic resonance signal output from the receiver coil 109 and to generate magnetic resonance data based on the detected magnetic resonance signal. More specifically, the receiver circuitry 110 is configured to generate the magnetic resonance signal by performing a digital conversion on the magnetic resonance signal output from the receiver coil 109. Further, the receiver circuitry 110 is configured to transmit the generated magnetic resonance data to the sequence controlling circuitry 120. Alternatively, the receiver circuitry 110 may be provided on the side of a gantry device including the static magnetic field magnet 101, the gradient coil 103, and the like.

The sequence controlling circuitry 120 is configured to perform an image taking process on the patient P, by driving the gradient power supply 104, the transmitter circuitry 108, and the receiver circuitry 110, based on sequence information transmitted thereto from the image processing apparatus 130. In this situation, the sequence information is information defining a procedure for performing the image taking process. The sequence information defines: the intensity of the electric current to be supplied by the gradient power supply 104 to the gradient coil 103 and the timing with which the electric current is to be supplied; the intensity of the RF pulse to be supplied by the transmitter circuitry 108 to the transmitter coil 107 and the timing with which the RF pulse is to be applied; the timing with which the magnetic resonance signal is to be detected by the receiver circuitry 110, and the like. For example, the sequence controlling circuitry 120 may be integrated circuitry such as an Application Specific Integrated Circuit (ASIC) or a Field Programmable Gate Array (FPGA), or electronic circuitry such as a Central Processing Unit (CPU) or a Micro Processing Unit (MPU). Details of pulse sequences executed by the sequence controlling circuitry 120 will be explained later.

Further, when having received the magnetic resonance data from the receiver circuitry 110, as a result of performing the image taking process on the patient P by driving the gradient power supply 104, the transmitter circuitry 108, and the receiver circuitry 110, the sequence controlling circuitry 120 transfers the received magnetic resonance data to the image processing apparatus 130.

The image processing apparatus 130 is configured to exercise overall control of the magnetic resonance imaging apparatus 100, to generate images, and the like. The image processing apparatus 130 includes a memory 132, an input device 134, a display 135, and processing circuitry 150. The processing circuitry 150 includes an interface function 131, a controlling function 133, and a generating function 136.

In the first embodiment, processing functions performed by the interface function 131, the controlling function 133, and the generating function 136 are stored in the memory 132 in the form of computer-executable programs. The processing circuitry 150 is a processor configured to realize the functions corresponding to the programs, by reading and executing the programs from the memory 132. In other words, the processing circuitry 150 that has read the programs has the functions illustrated within the processing circuitry 150 in FIG. 1. With reference to FIG. 1, the example is explained in which the single piece of processing circuitry (i.e., the processing circuitry 150) realizes the processing functions implemented by the interface function 131, the controlling function 133, and the generating function 136; however, another arrangement is also acceptable in which the processing circuitry 150 is structured by combining together a plurality of independent processors, so that the functions are realized as a result of the processors executing the programs. In other words, each of the functions described above may be configured as a program, so that the single piece of processing circuitry (i.e., the processing circuitry 150) executes the programs. In another example, one or more specific functions may be installed in dedicated independent program-executing circuitry. In FIG. 1, the interface function 131, the controlling function 133, and the generating function 136 are examples of a receiving unit, a controlling unit, a generating unit, and an analyzing unit, respectively. Further, the sequence controlling circuitry 120 is an example of the sequence controlling unit.

The term "processor" used in the above explanations denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 132.

Alternatively, instead of saving the programs in the memory 132, it is also acceptable to directly incorporate the programs in the circuitry of the one or more processors. In that situation, the one or more processors realize the functions by reading and executing the programs incorporated in the circuitry thereof. Similarly, the couch controlling circuitry 106, the transmitter circuitry 108, the receiver circuitry 110, and the like are also structured by using electronic circuitry such as the processors described above.

By employing the interface function 131, the processing circuitry 150 is configured to transmit the sequence information to the sequence controlling circuitry 120 and to receive the magnetic resonance data from the sequence controlling circuitry 120. Further, when having received the magnetic resonance data, the processing circuitry 150 including the interface function 131 is configured to store the received magnetic resonance data into the memory 132.

The magnetic resonance data stored in the memory 132 is arranged into a k-space by the controlling function 133. As a result, the memory 132 stores k-space data therein.

The memory 132 is configured to store therein the magnetic resonance data received by the processing circuitry 150 including the interface function 131, the k-space data arranged in the k-space by the processing circuitry 150 including the controlling function 133, image data generated by the processing circuitry 150 including the generating function 136, and the like. For example, the memory 132 is a semiconductor memory element such as a Random Access Memory (RAM) or a flash memory, or a hard disk, an optical disk, or the like.

The input device 134 is configured to receive various types of instructions and inputs of information from an operator. For example, the input device 134 may be a pointing device such as a mouse or a trackball, may be a selecting device such as a mode changing switch, or may be an inputting device such as a keyboard. Under control of the processing circuitry 150 including the controlling function 133, the display 135 is configured to display a Graphical User Interface (GUI) used for receiving an input of an image taking condition, an image generated by the processing circuitry 150 including the generating function 136, and the like. The display 135 is, for example, a display monitor such as a liquid crystal display monitor.

By employing the controlling function 133, the processing circuitry 150 is configured to exercise overall control of the magnetic resonance imaging apparatus 100 and to control image taking processes, image generating processes, image display processes, and the like. For example, the processing circuitry 150 including the controlling function 133 is configured to receive an input of the image taking condition (an image taking parameter or the like) through the GUI and to generate the sequence information according to the received image taking condition. Further, the processing circuitry 150 including the controlling function 133 is configured to transmit the generated sequence information to the sequence controlling circuitry 120.

By employing the generating function 136, the processing circuitry 150 is configured to generate an image by reading the k-space data from the memory 132 and performing a reconstruction process such as a Fourier transform on the read k-space data.

Next, a background of embodiments will be briefly explained.

Among magnetic resonance imaging schemes, imaging schemes using the Magnetization Transfer Contrast (MTC) effect are drawing attention. With the MTC effect, it is possible to observe an exchange of magnetism between free water protons and restricted protons in a polymer. It is therefore possible to render a composition of a tissue in an image.

As an example of the imaging schemes using the MTC effect, the so-called Chemical Exchange Saturation Transfer (CEST) method is known by which specific exchangeable protons are selectively saturated, so as to observe a free water signal after the saturation.

The CEST method, however, places a focus on a signal region related to the frequency region of offset frequencies that are usually in the range of approximately ±1,000 Hz compared to the frequency of the free water signal. Accordingly, no focus is placed on signal components having a width larger than the offset frequencies in the range of approximately ±1,000 Hz.

We shall analyze a Z-spectrum by using those signal components having a larger width. As a result of the analysis on the Z-spectrum, it was discovered that, with respect to the brain, the Z-spectrum includes a relatively long component related to (free) exchangeable protons (approximately 1,000 µs to 2,000 µs) and a relatively short component related to (restricted) exchangeable protons (approximately 20 µs to 40 µs). Based on this knowledge, we propose decomposing the Z-spectrum into a sum of a plurality of Lorentzian spectra and performed analyses.

In other words, the sequence controlling circuitry 120 is configured to execute a pulse sequence including application of an MT pulse. By employing the generating function 136, the processing circuitry 150 is configured to generate the Z-spectrum based on data obtained by executing the pulse sequence and to perform an analysis to decompose the Z-spectrum into the sum of a plurality of Lorentzian spectra.

In this situation, we discovered that, when the pulse sequence including the application of an MT pulse is executed after an action that causes a change in the physiological state of a patient, a change is exhibited in a parameter characterizing the Lorentzian spectra obtained when the Z-spectrum is decomposed into a sum of the plurality of Lorentzian spectra, in comparison to the situation where the pulse sequence including the application of an MT pulse is executed before the action. By using this finding, we implement a new magnetic resonance imaging scheme.

In this situation, the action that causes a physiological change in the patient is an action that causes the change in the physiological state on a slower time scale in comparison to an electrophysiological change in a neuron. Examples include an action of prompting the patient to take a deep breath, doing exercise, moving the head, or having a drug administered. Further, examples of the physiological change include a change between an awake state and a sleeping state. Existing MRI methods are not sufficiently sensitive to these small changes in the patient.

Based on the background explained above, the magnetic resonance imaging apparatus 100 according to the embodiment includes the sequence controlling circuitry 120 and the processing circuitry 150.

The sequence controlling circuitry 120 is configured to execute a first pulse sequence including application of an MT pulse and to subsequently execute a second pulse sequence including application of an MT pulse after an action that causes a change in the physiological state of the patient. By employing the generating function 136, the processing circuitry 150 is configured to generate a first Z-spectrum based on data obtained by executing the first pulse sequence, to generate a second Z-spectrum based on data obtained by executing the second pulse sequence, and to generate data by performing an analysis based on the first Z-spectrum and the second Z-spectrum.

Although it has hitherto been impossible with other MRI methods, it is now possible with this configuration to render in an image a very small impact on cerebral environment made by various changes in the physiological state of the patient such as doing exercise, moving the head, sleeping, taking a deep breath, having a drug administered, and the like. Further, the embodiment is not limited to the implementation on the brain. It is expected to be possible to perform the similar imaging process on other organs such as a myocardium, a kidney, the liver, or the like.

Next, details of the above configuration will be explained, with reference to FIGS. 2 to 6. FIG. 2 is a flowchart illustrating a processing procedure performed by the magnetic resonance imaging apparatus according to the first embodiment.

At first, at step S100, the sequence controlling circuitry 120 executes the first pulse sequence including application of an MT pulse (step S100).

In this situation, the MT pulse is an RF pulse having a frequency other than the frequency corresponding to the resonant frequency of free water protons. As a result of the application of the MT pulse, protons other than the free water protons become saturated. Because a chemical exchange is present between the protons other than the free water protons and the free water protons, magnetization of the protons other than the free water protons moves to the free water protons over the course of time.

In this situation, when an imaging process is performed by applying the RF pulse having the frequency corresponding to the resonant frequency of the free water protons, it is possible to indirectly render, in an image, the protons other than the free water protons excited by the MT pulse.

In other words, the first pulse sequence is structured with the application of the MT pulse and an acquisition sequence executed after the application of the MT pulse. Examples of the acquisition sequence include a two-dimensional (2D) or three-dimensional (3D) sequence used in a spiral or radial acquisition, and a sequence of Fast Spin Echo (FSE), Fast Advanced Spin Echo (FASE), or gradient echo; however, examples of the acquisition sequence are not limited to these examples.

During the first pulse sequence, the sequence controlling circuitry 120 performs the set made up of the application of the MT pulse and the acquisition sequence executed after the application of the MT pulse, multiple times while varying the frequency of the MT pulse little by little.

In this situation, for example, when a Chemical Exchange Saturation Transfer (CEST) imaging process is performed, the sequence controlling circuitry 120 would perform the acquisition by arranging the frequency of the applied MT pulse to be in a narrow frequency range, e.g., in the range of −5.0 ppm to +5.0 ppm with respect to the resonant frequency of the free water protons, by using a +0.5 ppm increment of frequency for the acquisition at each point. In contrast, in the magnetic resonance imaging apparatus 100 according to the present embodiment, for the purpose of acquiring the Z-spectrum in a wider frequency range, the sequence controlling circuitry 120 performs data acquisition, for example, in the range of −28,000 Hz to +31,000 Hz so as to acquire data with higher density at the frequencies in the vicinity of the resonant frequency of the free water protons and so as to acquire data with lower density at the frequencies away from the vicinity of the resonant frequency of the free water protons, while acquiring the data at the fifty frequencies in total, for example.

Subsequently, at step S110, an action that causes a change in the physiological state of the patient is taken.

In this situation, the action that causes the physiological change in the patient is a change caused in the physiological state on a slower time scale in comparison to an electrophysiological change in a neuron. For example, the action may be prompting the patient to take a deep breath, doing exercise, moving the head, or having a drug administered. In other words, at step S110, the patient takes a deep breath, does exercise, moves the head, or has the drug administered.

In another example, the physiological change may be, for example, a change between an awake state and a sleeping state. In other words, for example, the patient in a sleeping state at step S100 wakes up at step S110. Alternatively, the patient in an awake state at step S100 transitions into a sleeping state at step S110.

Subsequently, at step S120, the sequence controlling circuitry 120 executes the second pulse sequence to apply an MT pulse, after the action taken at step S110 to cause the change in the physiological state of the patient. The second pulse sequence executed by the sequence controlling circuitry 120 at step S120 is typically the same pulse sequence as the first pulse sequence executed by the sequence controlling circuitry 120 at step S100, except for the state of the patient; however, possible embodiments are not limited to this example.

Subsequently, at step S130, by employing the generating function 136, the processing circuitry 150 generates the first Z-spectrum based on the data obtained with respect to the plurality of frequencies by executing the first pulse sequence. In this situation, the Z-spectrum is a spectrum expressing the signal intensities that are observed when the RF pulse corresponding to the resonant frequency of the free water protons is applied after the application of the MT pulse, as a mathematical function of the frequency of the applied MT pulse.

Similarly, at step S150, by employing the generating function 136, the processing circuitry 150 generates the second Z-spectrum based on the data obtained with respect to the plurality of frequencies by executing the second pulse sequence.

In one example, at steps S130 and S140, by employing the generating function 136, the processing circuitry 150 generates the Z-spectra having offset frequencies in a wider range than the range of the analysis of the CEST effect, e.g., having frequencies in a range larger than ±1,000 Hz.

Subsequently, at step S150, by employing the generating function 136, the processing circuitry 150 generates data resulting from a Z-spectrum Analysis Protons (ZAP) analysis, by performing an analysis on the first Z-spectrum obtained at step S130 and the second Z-spectrum obtained at step S140.

In this situation, we discovered that it is possible to well fit each of the Z-spectra to a sum of two Lorentzian spectra, the Z-spectra being obtained at steps S130 and S140 and having the offset frequencies in the wider range than the range of the analysis of the CEST effect, e.g., having the frequencies in a range larger than ±1,000 Hz. In other words, by using Expression (1) presented below, it is possible to express a value y of each of the measured Z-spectra that has been normalized, where a component corresponding to a longer relaxation time period is referred to as a free (f) component, while a component corresponding to a shorter relaxation time period is referred to as a restricted (r) component.

$$y = F_f \frac{LW_f^2}{LW_f^2 + 4x^2} + F_r \cdot \frac{LW_r^2}{LW_r^2 + 4x^2} \quad (1)$$

In Expression (1), the letter x denotes the offset frequency of an MTC saturation pulse, while $LW_f$ and $LW_r$ denote Full-Width at Half-Maximum (FWHM) values of the free component and the restricted component, respectively. $F_f$ and $F_r$ denote the amplitude of the free component and the restricted component, respectively. In this situation, $F_f F_r = 1$ is satisfied. Apparent spin-spin relaxation time periods $T_{2,f}$ and $T_{2,r}$ of the free component and the restricted component, respectively, are each the reciprocal of the FWHM value, which can be calculated by using Expressions (2) and (3) presented below.

$$LW_f = 1/(\pi T_{2f}) \quad (2)$$

$$LW_r = 1/(\pi T_{2r}) \quad (3)$$

In other words, by employing the generating function 136, the processing circuitry 150 performs the analysis to decompose each of the Z-spectra into a sum of a plurality of Lorentzian spectra.

In one example, by employing the generating function 136, the processing circuitry 150 decomposes the first Z-spectrum obtained at step S130 into a sum of a plurality of first Lorentzian spectra and further calculates peak values ($F_f$ and $F_r$) and widths ($T_{2,f}$ and $T_{2,r}$) of the plurality of first Lorentzian spectra, based on the plurality of first Lorentzian spectra.

Further, by employing the generating function 136, the processing circuitry 150 decomposes the second Z-spectrum obtained at step S140 into a sum of a plurality of second Lorentzian spectra and further calculates peak values ($F_f$ and $F_r$) and widths or relaxation time periods ($T_{2,f}$ and $T_{2,r}$) of the plurality of second Lorentzian spectra, based on the plurality of second Lorentzian spectra.

FIGS. 3A to 3D illustrates examples of data obtained from this analysis. FIGS. 3A, 3B, 3C, and 3D are drawings illustrating the examples of images obtained by the magnetic resonance imaging apparatus according to the first embodiment. FIGS. 3A, 3B, 3C, and 3D illustrate an image indicating a peak value $F_f$ of a free component of a patient (male, age 67), an image indicating a peak value $F_r$ of a restricted component of the patient (male, age 67), an image indicating a peak value $F_f$ of a free component of a patient (female, age 27), and an image indicating a peak value $F_r$ of a restricted component of the patient (female, age 27), respectively. The data of the 67-year-old male patient and the data of the 27-year-old female patient are substantially similar to each other in the aspect of relative intensities of the signal intensities; however, in the data of the 27-year-old female patient, the area in which the peak value $F_f$ of the free component exhibits a large value (the area of the grey matter) and the areas in which the peak value $F_r$ of the restricted component exhibits a large value (the area of the white matter and the area of the central part of the grey matter) are larger than those in the data of the 67-year-old male patient. In this manner, by performing the analysis to decompose the Z-spectra generated at steps S130 and S140 into the sum of the plurality of Lorentzian spectra, the processing circuitry 150 generates the images such as the images indicating the peak value $F_f$ of the free component, the peak value $F_r$ of the restricted component, the relaxation time period $T_{2,r}$ of the restricted component, and the relaxation time period $T_{2,f}$ of the free component.

Next, a relationship between the action that causes a change in the physiological state of the patient and the obtained signal will be explained, with reference to FIGS. 4 and 5A to 5D.

For the purpose of checking to see how the ZAP analysis results obtained from the Z-spectra change before the action (hereinafter "pre-action") and after the action (hereinafter "post-action") that causes a change in the physiological state of the patient, the sequence controlling circuitry 120 performed an image taking process multiple times before and after an action 8 that caused a change in the physiological state of the patient. More specifically, during the action 8, the patient took a deep breath for 5 minutes. Further, before the action 8, the sequence controlling circuitry 120 performed a first pre-action image taking process 9 and a second pre-action image taking process 10. After the action 8, the sequence controlling circuitry 120 performed a first post-action image taking process 11 and a second post-action image taking process 12. The first pre-action image taking process 9, the second pre-action image taking process 10, the first post-action image taking process 11, and the second post-action image taking process 12 were performed by using mutually the same sequences each of which lasted seven and a half (7 and ½) minutes. In other words, including the time for taking the deep breath for 5 minutes, it took 35 minutes from the first pre-action image taking process 9 through the second post-action image taking process 12.

By comparing the data between the first pre-action image taking process 9 and the second pre-action image taking process 10, we checked reproducibility of the data.

FIGS. 5A, 5B, and 5C, and 5D illustrate examples of the obtained data. With respect to various image taking sites, FIGS. 5A, 5B, 5C, and 5D plot the relaxation time period $T_{2,f}$ of the free component, the peak value $F_f$ of the free component, the relaxation time period $T_{2,r}$ of the restricted component, and the peak value $F_r$ of the restricted component acquired from the second pre-action image taking process 10, the first post-action image taking process 11, and the second post-action image taking process 12.

Figure 5A:
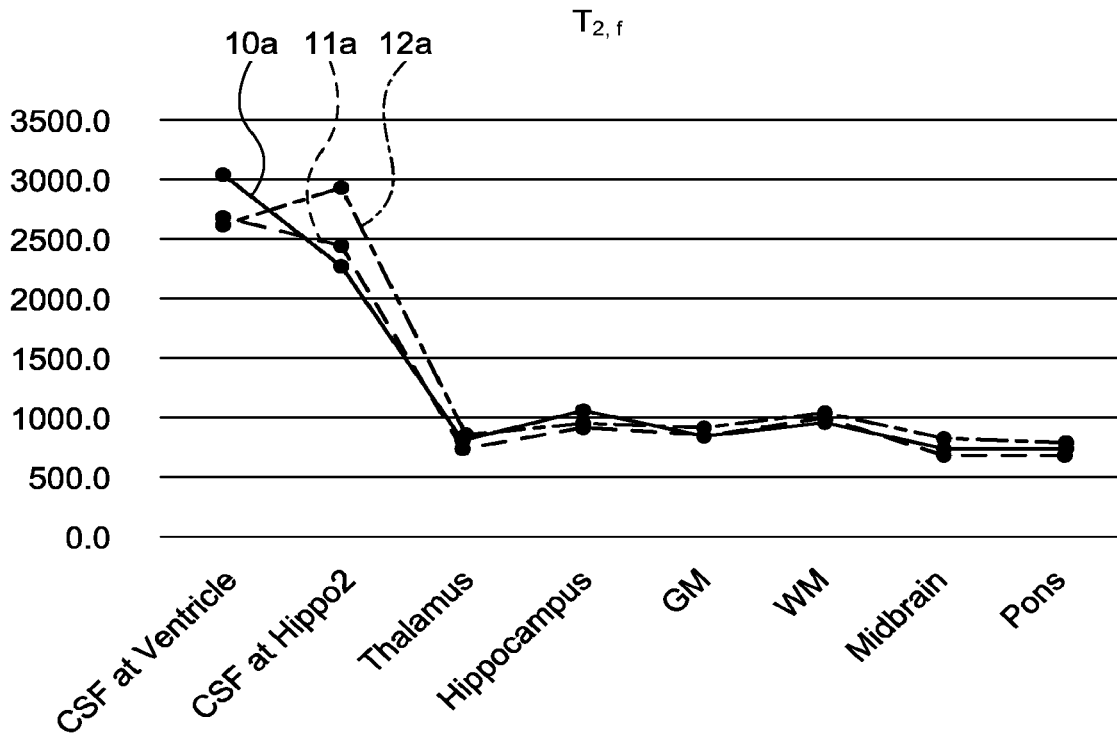
FIGS. 5A, 5B, 5C, and 5D are drawings illustrating examples of data obtained by the magnetic resonance imaging apparatus according to the first embodiment.

In other words, in FIG. 5A, with respect to the various sites, graphs 10a, 11a, and 12a plot the relaxation time period $T_{2,f}$ of the free component related to the second pre-action image taking process 10, the relaxation time period $T_{2,f}$ of the free component related to the first post-action image taking process 11, and the relaxation time period $T_{2,f}$ of the free component related to the second post-action image taking process 12, respectively.

Figure 5B:
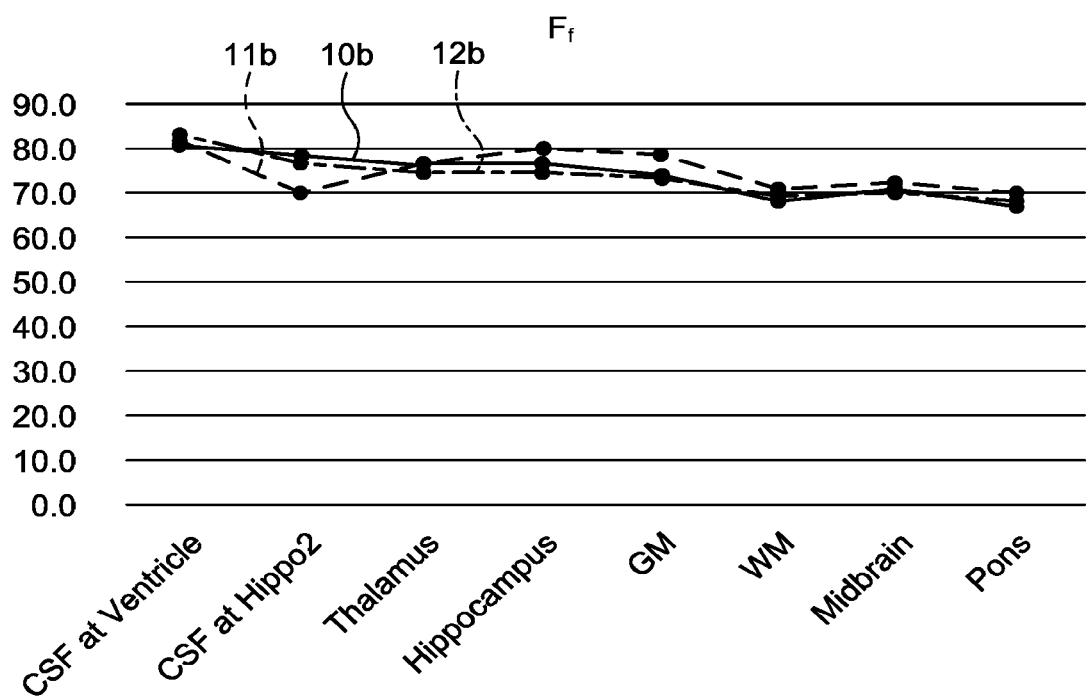

In FIG. 5B, with respect to the various sites, graphs 10b, 11b, and 12b plot the peak value $F_t$ of the free component related to the second pre-action image taking process 10, the peak value $F_f$ of the free component related to the first post-action image taking process 11, and the peak value $F_f$ of the free component related to the second post-action image taking process 12, respectively.

Figure 5C:
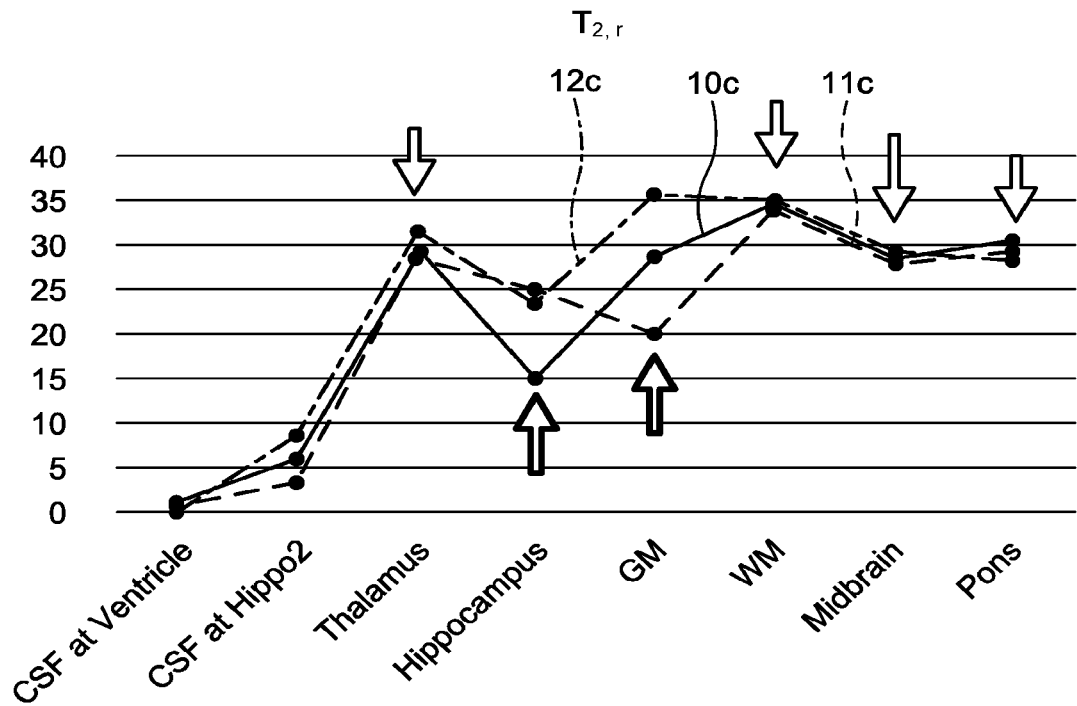

In FIG. 5C, with respect to the various sites, graphs 10c, 11c, and 12c plot the relaxation time period $T_{2,r}$ of the restricted component related to the second pre-action image taking process 10, the relaxation time period $T_{2,r}$ of the restricted component related to the first post-action image taking process 11, and the relaxation time period $T_{2,r}$ of the restricted component related to the second post-action image taking process 12, respectively.

Figure 5D:
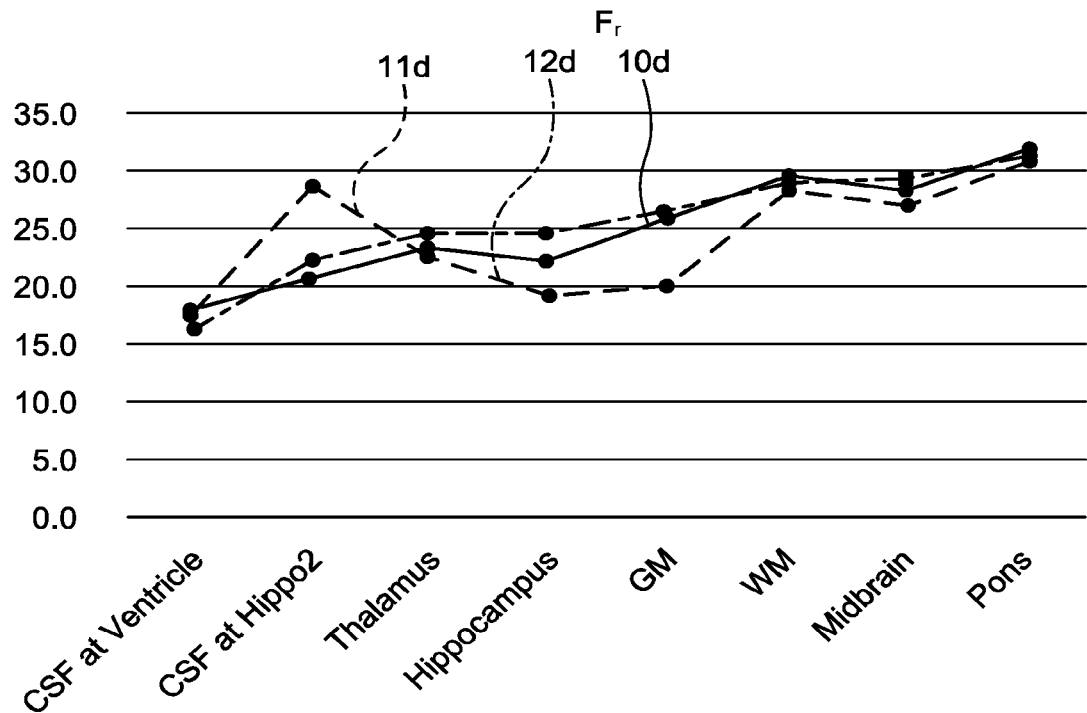

In FIG. 5D, with respect to the various sites, graphs 10d, 11d, and 12d plot the peak value $F_r$ of the restricted component related to the second pre-action image taking process 10, the peak value $F_r$ of the restricted component related to the first post-action image taking process 11, and the peak value $F_r$ of the restricted component related to the second post-action image taking process 12, respectively.

It is observed from FIGS. 5A to 5D that with respect to the hippocampus and the grey matter, the relaxation time periods $T_{2,\ r}$ of the restricted component significantly changed between before and after the action 8 and that with respect to the thalamus, the white matter, and the pons, the relaxation time periods $T_{2,\ r}$ of the restricted component did not exhibit significant changes. Accordingly, it is possible to arrive at a conclusion that, due to an impact of the action 8, there was a change in the relaxation time periods $T_{2,\ r}$ of the restricted component, with respect to the hippocampus and the grey matter.

Consequently, by employing the generating function 136, the processing circuitry 150 is configured to generate the data by performing a difference calculating process between the data (e.g., the peak values ($F_t$ and $F_r$) and the widths or the relaxation time periods ($T_{2,\ f}$ and $T_{2,\ r}$) of the plurality of Lorentzian spectra) obtained by performing the ZAP analysis on the first Z-spectrum and the data (similarly, e.g., the peak values ($F_f$ and $F_r$) and the widths or the relaxation time periods ($T_{2,\ f}$ and $T_{2,\ r}$) of the plurality of Lorentzian spectra) obtained by performing the ZAP analysis on the second Z-spectrum. As a result, it is possible to render, in a magnetic resonance image, the impact made by the action that causes the change in the physiological state on a slower time scale in comparison to an electrophysiological change in a neuron.

Subsequently, at step S160, by employing the controlling function 133, the processing circuitry 150 causes the display 135 to display the data obtained at step S150.

Let us further explain the process of checking the reproducibility of the data. To check the reproducibility of the data, it is possible to use a Coefficient of Variation (CV), for example, in addition to comparing the data between the first pre-action image taking process 9 and the second pre-action image taking process 10.

In this situation, for example, as coefficients of variation, a value obtained by dividing a standard deviation between the second pre-action image taking process 10 and the first pre-action image taking process 9 by an average of the second pre-action image taking process 10 and the first pre-action image taking process 9 and further multiplying the result by 100 will be referred to as R1; a value obtained by dividing a standard deviation between the first post-action image taking process 11 and the second pre-action image taking process 10 by an average of the first post-action image taking process 11 and the second pre-action image taking process 10 and further multiplying the result by 100 will be referred to as R2; a value obtained by dividing a standard deviation between the second post-action image taking process 12 and the first post-action image taking process 11 by an average of the second post-action image taking process 12 and the first post-action image taking process 11 and further multiplying the result by 100 will be referred to as R3; and a value obtained by dividing a standard deviation between a third post-action image taking process 13 and the second post-action image taking process 12 by an average of the third post-action image taking process 13 and the second post-action image taking process 12 and further multiplying the result by 100 will be referred to as R4.

Figure 6:
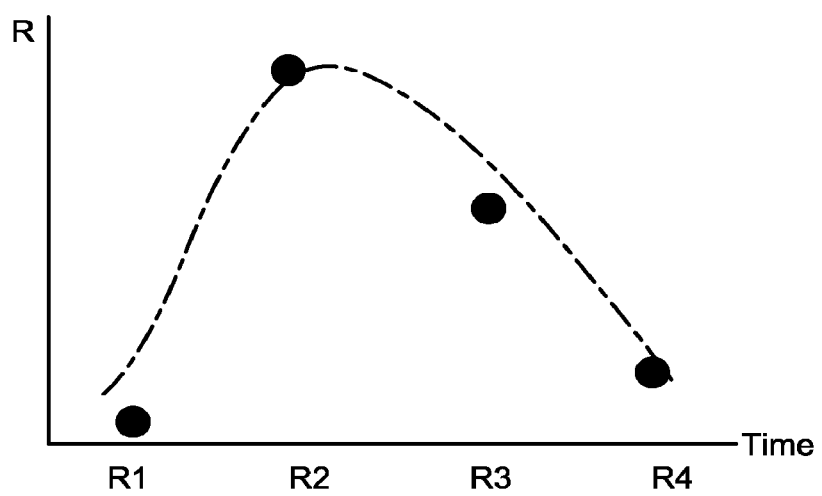
FIG. 6 is a drawing illustrating another process performed by the magnetic resonance imaging apparatus according to the first embodiment.

Typically, behaviors of the coefficients of variation R1, R2, R3, and R4 exhibit a form as illustrated in FIG. 6. When the coefficients of variation R1, R2, R3, and R4 behave in this manner, because R1 is the coefficient of variation related to the pieces of data that are both pre-action, it is possible to use R1 as a reference for judging the reproducibility of the data. Further, because the coefficient of variation R2 is larger than R1, it is observed that an effect of the action is exhibited. Further, the coefficient of variation R3 is still larger than R1, and the effect of the action reaches a peak in the vicinity thereof. Further, the coefficient of variation R4 reaches approximately a baseline in comparison to R1, and it is expected that no significant change in the data will thereafter be made by the action.

Further, as another method for checking the reproducibility of the data, it is also acceptable to simply plot the signal intensities for the pre-action and the post-action.

As explained above, the magnetic resonance imaging apparatus according to the first embodiment is capable of performing the magnetic resonance imaging process related to the change in the physiological state of the patient.

Second Embodiment

In a second embodiment, various methods for displaying the results of the Z-spectrum analyses and relevant GUIs will be explained.

Figure 7:
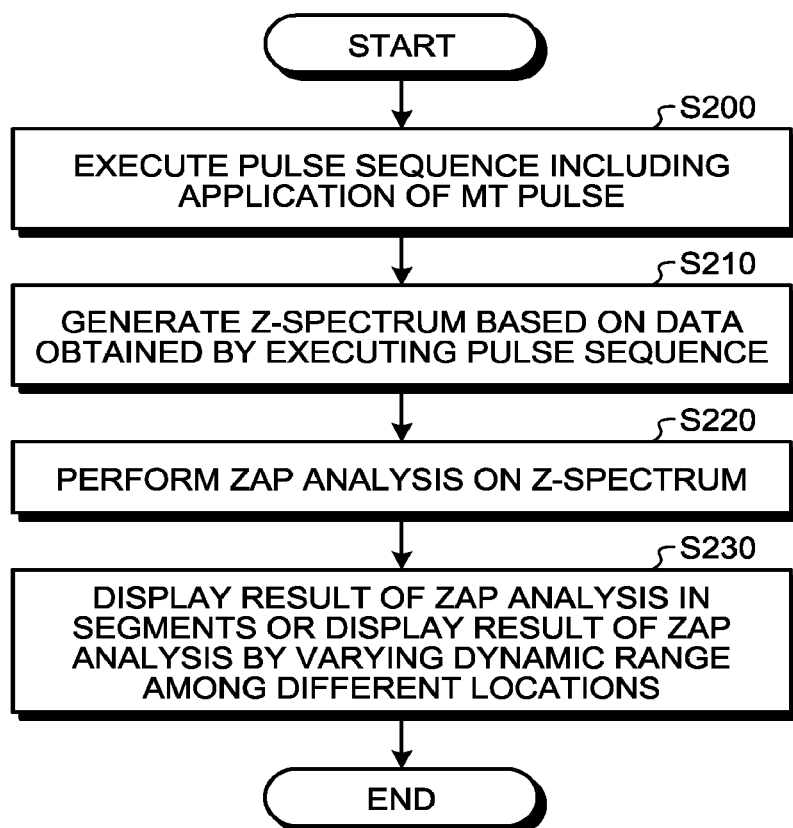
FIG. 7 is a flowchart illustrating a processing procedure performed by a magnetic resonance imaging apparatus according to a second embodiment.

FIG. 7 is a flowchart illustrating a processing procedure performed by a magnetic resonance imaging apparatus according to the second embodiment.

In the first embodiment, the example is explained in which the sequence controlling circuitry 120 executes the pulse sequence twice in total, namely before and after the action that causes the change in the physiological state of the patient; however, as for the second embodiment, possible embodiments are not limited to the example in which the pulse sequence is executed twice. The pulse sequence may be executed only once.

At first, at step S100, the sequence controlling circuitry 120 executes a pulse sequence including application of an MT pulse (step S200).

Similarly to the first embodiment, the pulse sequence is structured with the application of the MT pulse and the acquisition sequence executed after the application of the MT pulse. Examples of the acquisition sequence include a 2D or 3D sequence used in a spiral or radial acquisition, and a sequence of Fast Spin Echo (FSE), Fast Advanced Spin Echo (FASE), or gradient echo; however, examples of the acquisition sequence are not limited to these examples.

Similarly to the first embodiment, during the first pulse sequence, the sequence controlling circuitry 120 performs the set made up of the application of the MT pulse and the acquisition sequence executed after the application of the MT pulse, multiple times while varying the frequency of the MT pulse little by little.

Subsequently, at step S210, by employing the generating function 136, the processing circuitry 150 generates a Z-spectrum based on data obtained with respect to a plurality of frequencies by executing the pulse sequence at step S200.

After that, at step S220, by employing the generating function 136, the processing circuitry 150 generates data (an image) resulting from a Z-spectrum Analysis Protons (ZAP) analysis, by performing an analysis on the Z-spectrum obtained at step S210. More specifically, by employing the generating function 136, the processing circuitry 150 performs the analysis to decompose the obtained Z-spectrum into a sum of a plurality of spectra and generates the data (the image) resulting from the ZAP analysis based on at least one selected from among the intensities, the widths, and the relaxation time periods of the plurality of spectra.

Subsequently, at step S230, by employing the controlling function 133, the processing circuitry 150 causes the display 135 to display the image generated at step S220 as a result of the ZAP analysis, while the image is divided into a plurality of segments. Further, when necessary, by employing the controlling function 133, the processing circuitry 150 causes the display 135 to display the plurality of segments by using mutually-different dynamic ranges.

Figure 8A:
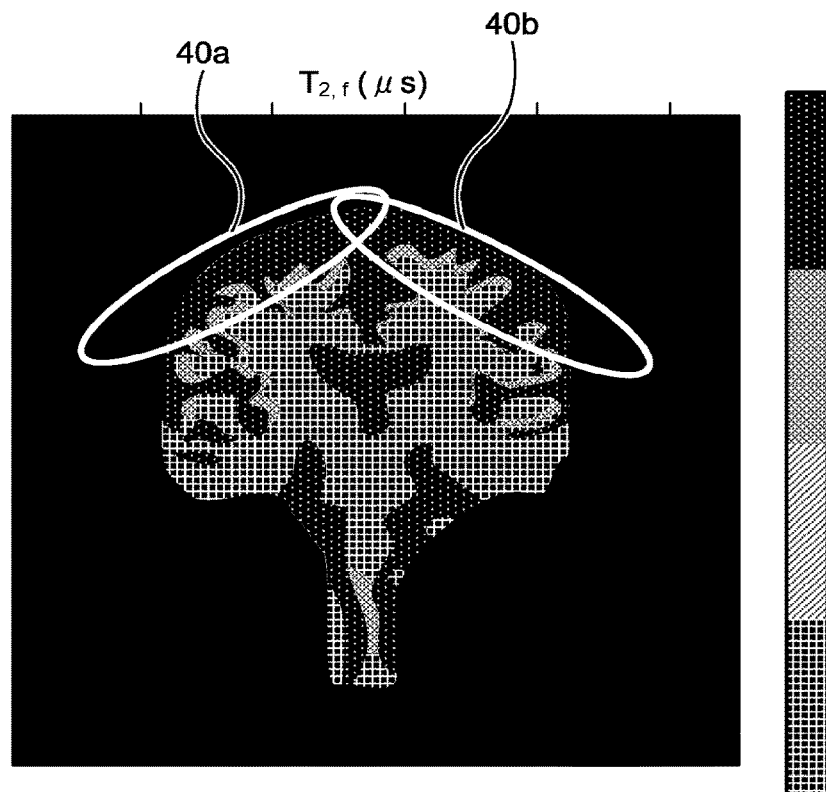
FIG. 8A, 8B, and 8C are drawings illustrating examples of images which the magnetic resonance imaging apparatus according to the second embodiment causes a display to display.
Figure 8B:
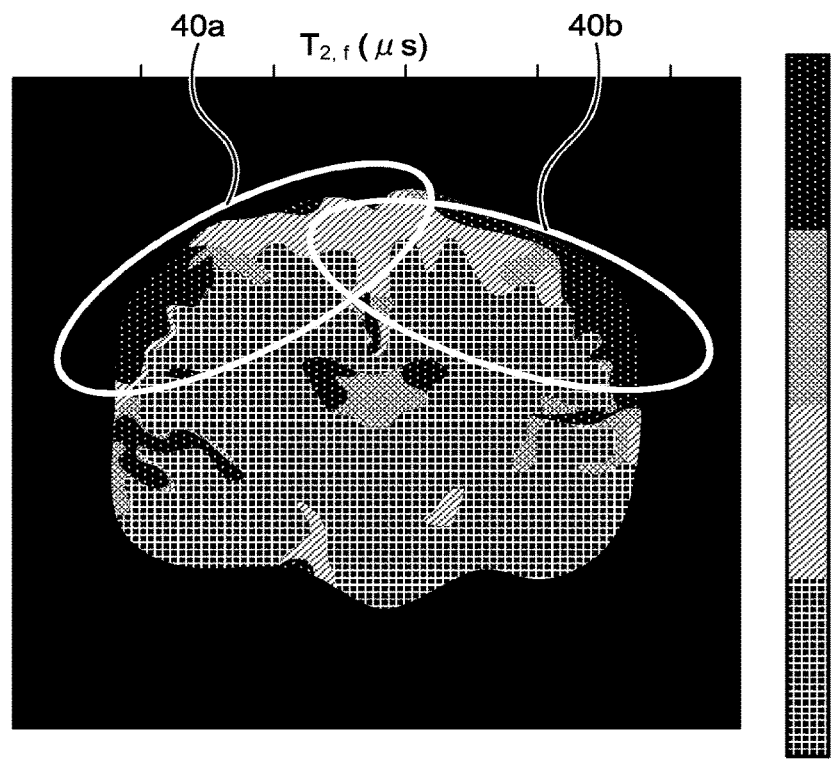

First of all, a background for dividing the image into the plurality of segments and varying the dynamic range among the segments will be explained, with reference to FIGS. 8A and 8B. FIGS. 8A and 8B both display a relaxation time period $T_{2,f}$ of a free component on a coronal cross-section of the brain of mutually the same volunteer person, but in mutually-different dynamic ranges. More specifically, the dynamic range in the display in FIG. 8A is 500 μs to 1,800 μs. In contrast, the dynamic range in the display in FIG. 8B is 500 μs to 3,000 μs. Further, regions 40a and 40b are regions of Cerebrospinal Fluid (CSF).

In this situation, with the dynamic range in FIG. 8A, although the contrast of the cerebral parenchyma is clear, signal values of the CSF in the regions 40a and 40b partially exceed beyond the dynamic range. In contrast, with the dynamic range in FIG. 8B, although the contrast of the CSF is clear, the contrast of the cerebral parenchyma is unclear. Accordingly, when the relaxation time period $T_{2,f}$ of the free component on a coronal cross-section of the brain is to be displayed, for example, it is desirable, for the purpose of properly rendering the plurality of sites in a single image, to cause the display 135 to display the image by using the mutually-different dynamic ranges for the plurality of segments.

In view of the background explained above, by employing the controlling function 133, the processing circuitry 150 causes the display 135 to display the image generated by performing the ZAP analysis on the Z-spectrum, by using the mutually-different dynamic ranges for the plurality of segments.

Figure 8C:
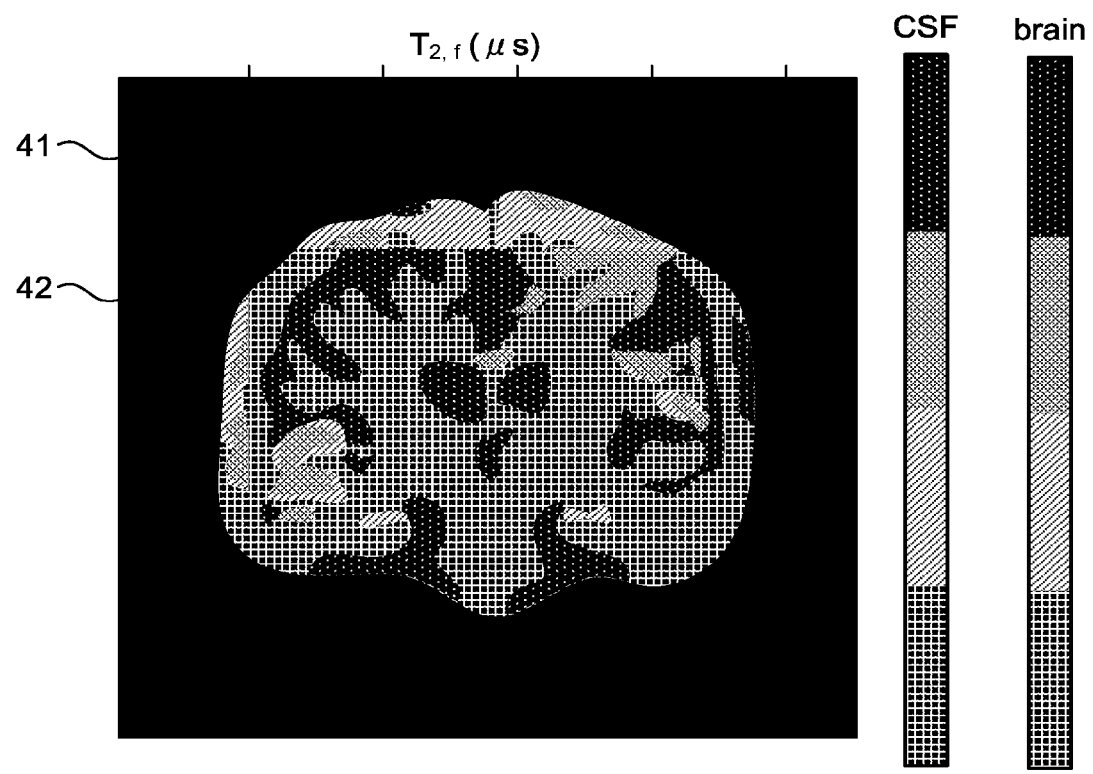

FIG. 8C illustrates an example of the above situation. FIG. 8C is a drawing illustrating an example of an image which a magnetic resonance imaging apparatus according to the second embodiment causes the display to display. By employing the controlling function 133, the processing circuitry 150 arranges the relaxation time $T_{2,f}$ of the free component on a coronal cross-section of the brain to be displayed, by dividing the CSF region into a plurality segments, namely a segment 41 and a segment 42, and further causing the display 135 to display the CSF while varying the dynamic range among the plurality of segments resulting from the division. For example, by employing the controlling function 133, the processing circuitry 150 causes the display 135 to display the relaxation time $T_{2,f}$ of the free component on the coronal cross-section of the brain, by using a dynamic range of 500 μs to 3,000 μs for the segment 41 where the contrast of the CSF is important and using a dynamic range of 600 μs to 1,800 μs for the segment 42 where the contrast of the cerebral parenchyma is important.

In this situation, by employing the controlling function 133, the processing circuitry 150 may receive a dynamic range for each of the plurality of segments resulting from the division, through the input device 134. Alternatively, by employing the controlling function 133, the processing circuitry 150 may automatically calculate a dynamic range for each of the plurality of segments resulting from the division, based on signal values of the image to be output.

FIG. 9 illustrates an example of a GUI related to the adjustments of the dynamic ranges. FIG. 9 is a drawing illustrating the example of the GUI related to the magnetic resonance imaging apparatus according to the second embodiment.

By employing the controlling function 133, the processing circuitry 150 receives a setting of a Region of Interest (ROI) from a user. For example, by employing the controlling function 133, the processing circuitry 150 receives a setting for the size and the location of the segment 41 from the user, via buttons 43a, 43b, 43c, 43d, 43e, 43f, 43g, and 43h, or the like. Further, by employing the controlling function 133, the processing circuitry 150 receives a setting for the size and the location of the segment 42 from the user, via buttons 44a, 44b, 44c, 44d, 44e, 44f, 44g, and 44h, or the like.

Further, by employing the controlling function 133, the processing circuitry 150 receives a change in the dynamic range used for the display of the segment 41 from the user, via buttons 45a, 45b, 45c, and 45d, or the like. Further, by employing the controlling function 133, the processing circuitry 150 receives a change in the dynamic range used for the display of the segment 42 from the user, via buttons 46a, 46b, 46c, and 46d, or the like.

Figure 10A:
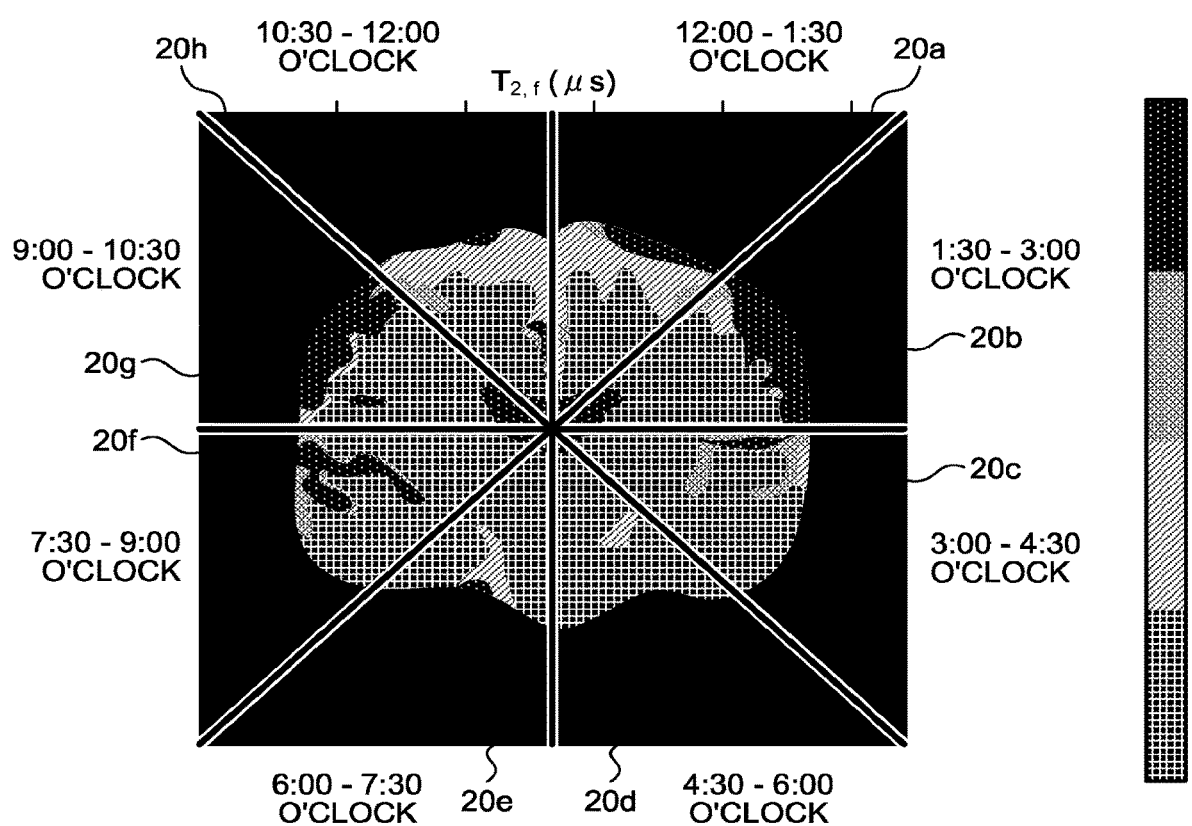
FIGS. 10A, 10B, and 10C are drawings illustrating examples of images which the magnetic resonance imaging apparatus according to the second embodiment causes a display to display.
Figure 10B:
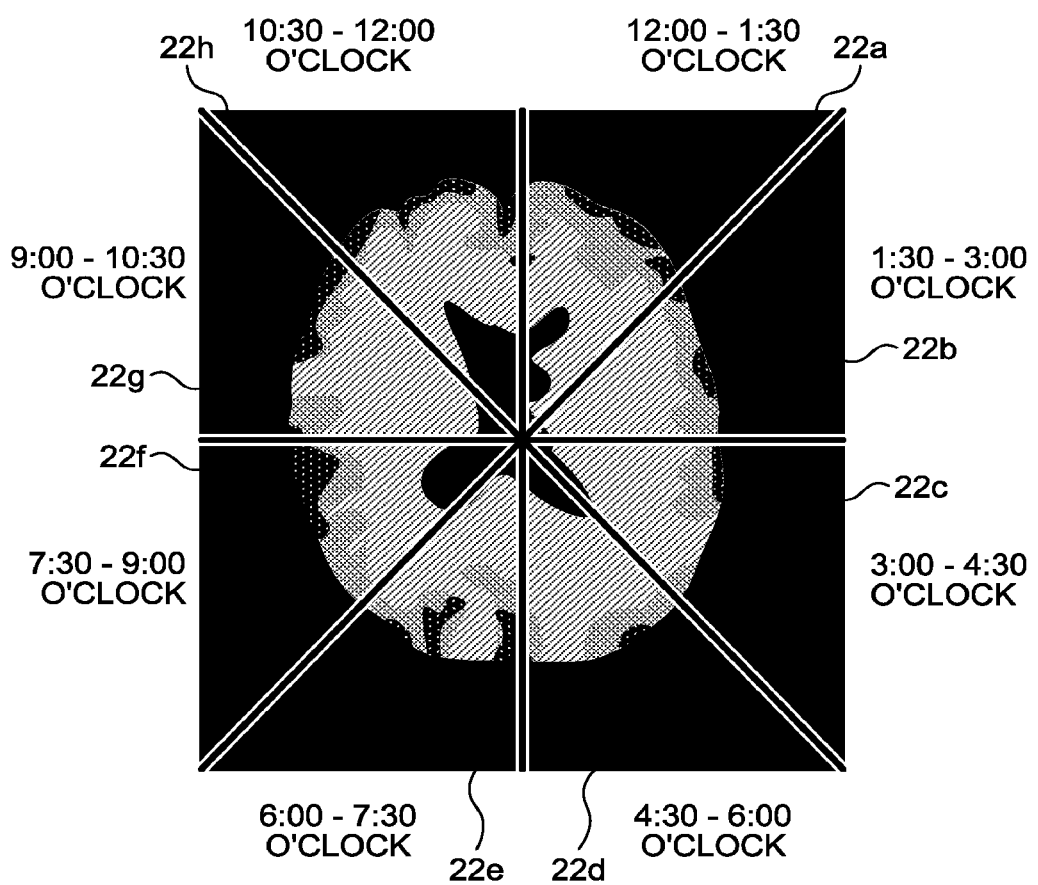
Figure 10C:
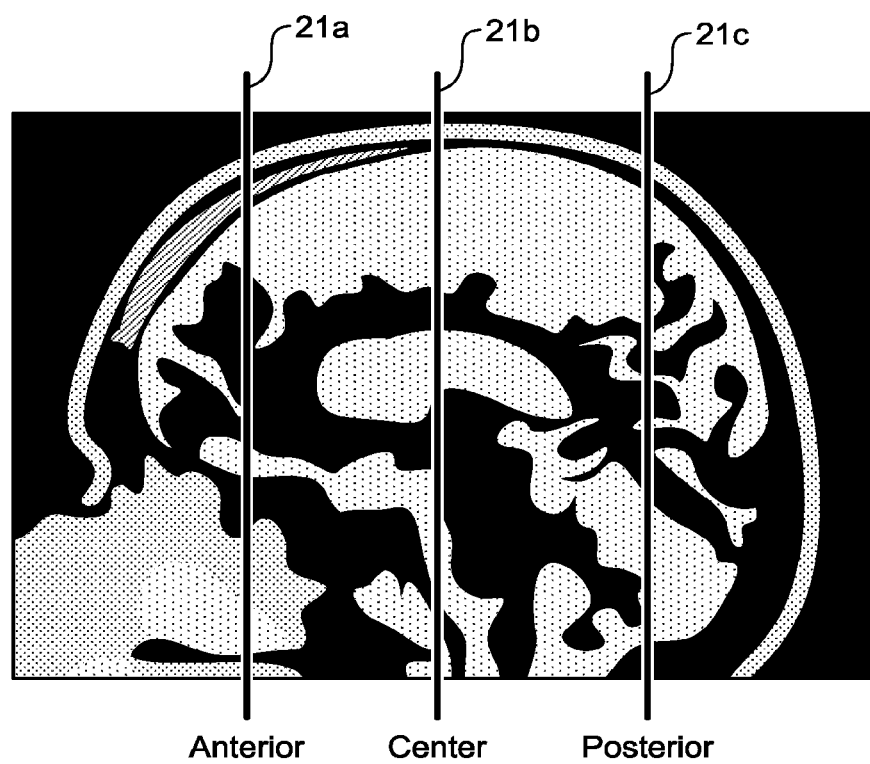

Next, an example will be explained in which an image is radially divided into segments by using a predetermined feature point as the center, with reference to FIGS. 10A and 10B. FIGS. 10A and 10B illustrate examples of the segmentation. FIG. 10A illustrates an example in which a relaxation time period $T_{2,f}$ of the free component on a coronal cross-section of the brain taken at a center part 21b of the sagittal image in FIG. 10C is radially divided into a plurality of segments. More specifically, by employing the controlling function 133, the processing circuitry 150 causes the display 135 to display the relaxation time period $T_{2,f}$ of the free component on the coronal cross-section, in the plurality of segments that are radially divided while using the lateral ventricle serving as a feature point as the center. In one example, by employing the controlling function 133, the processing circuitry 150 causes the display 135 to display the relaxation time period $T_{2,f}$ of the free component on the coronal cross-section, in the plurality of segments that are divided while using the lateral ventricle serving as a feature point as the center, the segments namely being: a segment 20a in the 12:00-1:30 o'clock direction, a segment 20b in the 1:30-3:00 o'clock direction, a segment 20c in the 3:00-4:30 o'clock direction, a segment 20d in the 4:30-6:00 o'clock direction, a segment 20e in the 6:00-7:30 o'clock direction, a segment 20f in the 7:30-9:00 o'clock direction, a segment 20g in the 9:00-10:30 o'clock direction, and a segment 20h in the 10:30-12:00 o'clock direction. Further, by employing the controlling function 133, the processing circuitry 150 causes the display 135 to display, when necessary, an image generated by performing a ZAP analysis on the Z-spectrum by using mutually-different dynamic ranges for the plurality of segments.

In this situation, for example, in the segment 20a in the 12:00-1:30 o'clock direction, because it is important to properly render the CSF, the dynamic range is set to 500 μs to 3,000 μs, for example. As another example, in the segments 20c, 20d, 20e, and 20f in the 3:00-9:00 o'clock direction, because it is important to properly render the cerebral parenchyma, the dynamic range is set to 600 μs to 1,800 μs, for example. By setting the mutually-different dynamic ranges for the plurality of segments, it is possible to properly render the various sites in the single image, which enhances the user's experience.

In the embodiment above, the example is explained in which the coronal cross-section is a coronal cross-section taken at the center part 21b of the sagittal image in FIG. 10C; however, possible embodiments are not limited to this example. It is possible to perform the same process by using a coronal cross-section taken at an anterior part 21a or a posterior part 21c of the sagittal image in FIG. 10C, for example.

Although similar to FIG. 10A, FIG. 10B illustrates an example in which a relaxation time period $T_{2,f}$ of the free component on an axial cross-section, instead of the coronal cross-section, is radially divided into a plurality of segments. More specifically, by employing the controlling function 133, the processing circuitry 150 causes the display 135 to display the relaxation time period $T_{2,f}$ of the free component on the axial cross-section, in the plurality of segments that are radially divided while using the lateral ventricle serving as a feature point as the center. In one example, by employing the controlling function 133, the processing circuitry 150 causes the display 135 to display the relaxation time period $T_{2,f}$ of the free component on the axial cross-section, in the plurality of segments that are divided while using the lateral ventricle serving as a feature point as the center, the segments namely being: a segment 22a in the 12:00-1:30 o'clock direction, a segment 22b in the 1:30-3:00 o'clock direction, a segment 22c in the 3:00-4:30 o'clock direction, a segment 22d in the 4:30-6:00 o'clock direction, a segment 22e in the 6:30-7:30 o'clock direction, a segment 22f in the 7:30-9:00 o'clock direction, a segment 22g in the 9:00-10:30 o'clock direction, and a segment 22h in the 10:30-12:00 o'clock direction. Further, by employing the controlling function 133, the processing circuitry 150 causes the display 135 to display, when necessary, an image generated by performing a ZAP analysis on the Z-spectrum by using mutually-different dynamic ranges for the plurality of segments.

Figure 11:
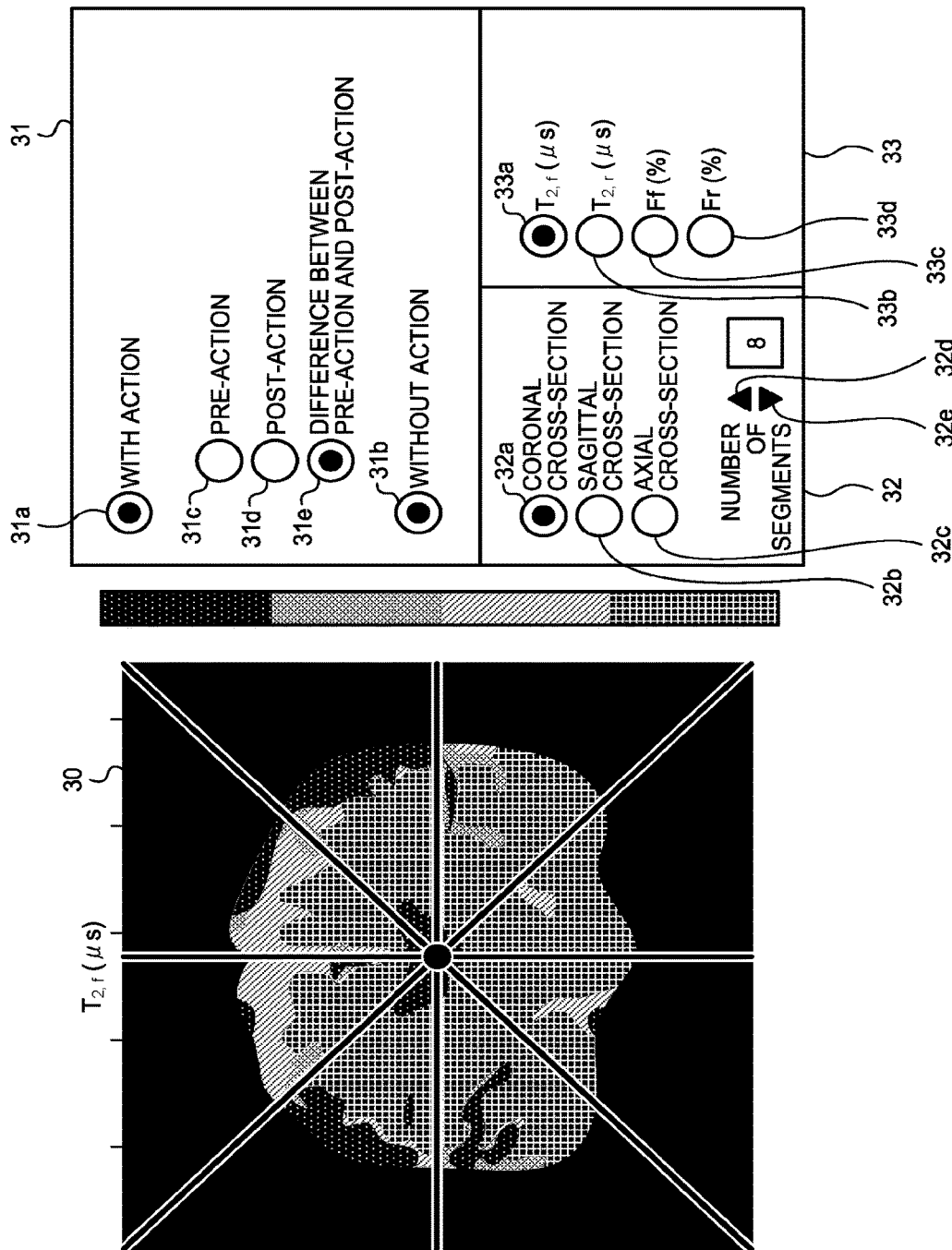
FIG. 11 is a drawing illustrating another example of the Graphical User Interface (GUI) related to the magnetic resonance imaging apparatus according to the second embodiment.

FIG. 11 illustrates an example of a Graphical User Interface (GUI) related to the magnetic resonance imaging apparatus according to the second embodiment.

By employing the controlling function 133, the processing circuitry 150 receives, via the input device 134, an input from the user indicating which of the images generated by performing the ZAP analysis is to be displayed on the display 135, via buttons 33a, 33b, 33c, and 33d provided in a display panel 33 displayed on the display 135. The image specified by the received input will be displayed in a panel 30.

Further, by employing the controlling function 133, the processing circuitry 150 receives from the user, via the input device 134, a setting about a displayed cross-section via buttons 32a, 32b, and 32c in a display panel 32 displayed on the display 135, as well as a setting related to the number of divided segments via buttons 32d and 32e.

Further, by employing the controlling function 133, the processing circuitry 150 receives from the user, via the input device 134, a setting about whether the image taking process related to the current display includes an image taking process performed by including an action that causes a change in the physiological state of the patient, via buttons 31a and 31b in the display panel 31 displayed on the display 135. When the image taking process includes an image taking process performed by including an action that causes a change in the physiological state of the patient, as explained later, the processing circuitry 150 receives, by employing the controlling function 133, a setting from the user, via the input device 134, indicating which image is to be displayed from among a pre-action image, a post-action image, a difference image between the pre-action and the post-action, via buttons 31c, 31d, and 31e.

Similarly to the first embodiment, in the second embodiment also, the sequence controlling circuitry 120 may execute pulse sequences before and after the action that causes the change in the physiological state of the patient.

Figure 12:
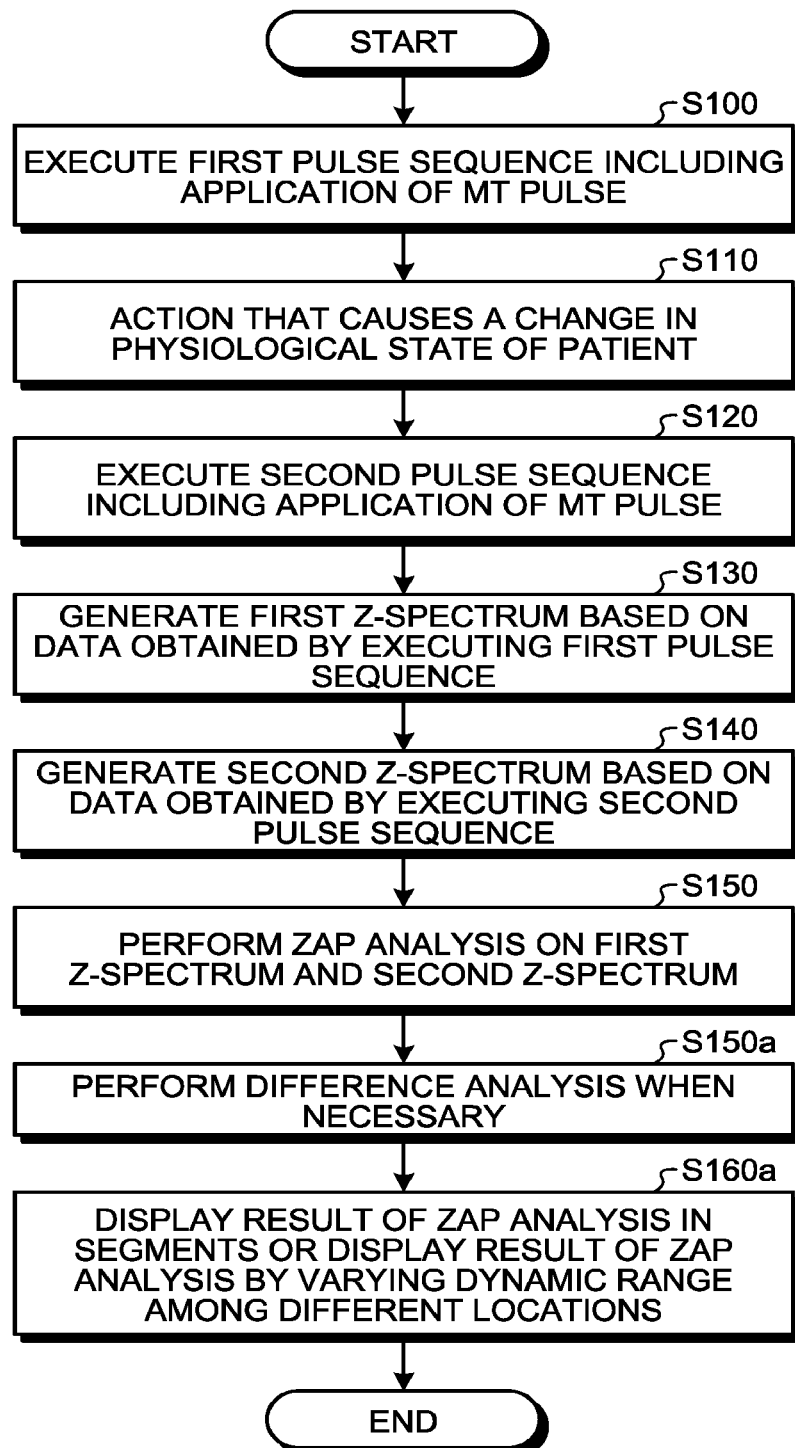
FIG. 12 is a flowchart illustrating a processing procedure performed by the magnetic resonance imaging apparatus according to the second embodiment.

FIG. 12 illustrates a procedure of the processes described above. Because the processes at steps S100 through S150 are the same as the processes explained at steps S100 through S150 with reference to FIG. 2 in the first embodiment, duplicate explanations thereof will be omitted.

At step S150a, by employing the generating function 136, the processing circuitry 150 generates, when necessary, an image to be output by performing a difference calculating process between data obtained by performing a ZAP analysis on the first Z-spectrum and data obtained by performing a ZAP analysis on the second Z-spectrum. For example, by performing a difference calculating process between the peak value $F_f$ of the free component, the peak value $F_r$ of the restricted component, the relaxation time period $T_{2,r}$ of the restricted component, and the relaxation time period $T_{2,r}$ of the free component obtained by performing the analysis on the first Z-spectrum; and the peak value $F_f$ of the free component, the peak value $F_r$ of the restricted component, the relaxation time period $T_{2,r}$ of the restricted component, and the relaxation time period $T_{2,r}$ of the free component obtained by performing the analysis on the second Z-spectrum, respectively, the processing circuitry 150 generates a difference image of the peak values $F_f$ of the free component, a difference image of the peak values $F_r$ of the restricted component, a difference image of the relaxation time periods $T_{2,r}$ of the restricted component, and a difference image of the relaxation time periods $T_{2,f}$ of the free component, the differences being found between before the action and after the action.

Subsequently, at step S160a, by employing the controlling function 133, the processing circuitry 150 causes the display 135 to display either the analysis result obtained at step S150 or the analysis result obtained at step S150a, by dividing the result into a plurality of segments. Further, when necessary, by employing the controlling function 133, the processing circuitry 150 causes the display 135 to display the analysis result for each of the plurality of segments, by varying the dynamic range among different locations.

Alternatively, by employing the controlling function 133, the processing circuitry 150 may cause the display 135 to display the analysis result, in a table format instead of the image format. An example of such a table is illustrated in FIG. 13. For example, by employing the controlling function 133, the processing circuitry 150 causes the display 135 to display, in the table format, parameters of the ZAP analysis results corresponding to the segments that are radially divided while using the lateral ventricle serving as a feature point as the center, as well as the differences between before the action and after the action, for each of the segments on a coronal cross-section and an axial cross-section at the center position in a sagittal image.

As explained above, the magnetic resonance imaging apparatus according to the second embodiment is able to enhance the user's experience.

Computer Programs

It is possible to execute the instructions described in the processing procedure explained in the above embodiments, based on a computer program (hereinafter, simply "program") realized with software. By having a generic computer store therein the program in advance and read the program, it is also possible to achieve the same advantageous effects as those achieved by the magnetic resonance imaging apparatus 100 according to the above embodiments.

The instructions described in the above embodiments are recorded, as a computer-executable program, onto a magnetic disk (e.g., a flexible disk, a hard disk), an optical disk (e.g., a Compact-Disk Read-Only Memory [CD-ROM], a Compact Disk Recordable [CD-R], a Compact Disk Rewritable [CD-RW], a Digital Versatile Disk Read-Only Memory [DVD-ROM], DVD±Recordable [DVD±R], DVD±Rewritable [DVD±R]), a semiconductor memory, or a similar recording medium. Any storage format may be used as long as a computer or an embedded system is able to read data from the storage medium. The computer is able to realize the same operations as those performed by the magnetic resonance imaging apparatus 100 according to the above embodiments, by reading the program from the recording medium and causing a CPU to execute the instructions written in the program based on the read program. Further, when obtaining or reading the program, the computer may obtain or read the program via a network.

Further, based on the instructions in the program installed from the storage medium into a computer or an embedded system, an Operating System (OS) working in the computer, database management software, or middleware (MW) such as a network may execute a part of the processes that realize the above embodiments. Further, the storage medium does not necessarily have to be a medium independent of the computer or the embedded system. The storage medium may be a storage medium that downloads and stores therein or temporarily stores therein the program transferred via a Local Area Network (LAN) or the Internet. Further, the storage medium being used does not necessarily have to be one. Examples of the storage medium of the present embodiments include the situation where the processes in the above embodiments are executed from a plurality of media. It is possible to use any configuration as the configuration of the medium/media.

The computer or the embedded system in the above embodiments is configured to execute the processes described in the above embodiments based on the program stored in the one or more storage media and may have any configuration such as a single apparatus (e.g., a personal computer, a microcomputer) or a system in which a plurality of apparatuses are connected together via a network. Further, the term "computer" in the above embodiments does not necessarily denote a personal computer and may be an arithmetic processing apparatus or a microcomputer included in an information processing device. The term "computer" is a generic name for any device or apparatus capable of realizing the functions in the above embodiments by using one or more programs.

By using the magnetic resonance imaging apparatus according to at least one aspect of the embodiments described above, it is possible to perform the magnetic resonance imaging process related to the change in the physiological state of the patient. Also, by using the display method according to at least one aspect of the embodiments described above, it is possible to enhance the user's experience.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured:
   to generate an image by performing an analysis based on a Z-spectrum generated based on data obtained by executing a pulse sequence including application of a Magnetization Transfer (MT) pulse; and
   to cause a display to display the generated image by dividing the image into a plurality of segments and using mutually-different dynamic ranges for the plurality of segments.

2. The image processing apparatus according to claim 1, wherein the processing circuitry is configured to divide a region of Cerebrospinal Fluid (CSF) into the plurality of segments and cause the display to display the CSF by varying the dynamic range among the plurality of segments resulting from the division.

3. The image processing apparatus according to claim 1, wherein the plurality of segments are segments that are radially divided while using a feature point as a center.

4. The image processing apparatus according to claim 1, wherein the processing circuitry is further configured to:
   perform the analysis to decompose the Z-spectrum into a sum of a plurality of spectra, and
   generate the image based on at least one selected from between intensities and widths of the plurality of spectra.

5. The image processing apparatus according to claim 1, wherein the processing circuitry is further configured to generate the image based on: a first Z-spectrum generated based on data obtained by executing a first pulse sequence including application of a Magnetization Transfer (MT) pulse; and a second Z-spectrum generated based on data obtained by executing, after the execution of the first pulse sequence, a second pulse sequence including application of an MT pulse after an action that causes a change in a physiological state of a patient.

6. The image processing apparatus according to claim 5, wherein the processing circuitry is further configured to generate the image by performing a difference calculating process between data obtained by performing the analysis on the first Z-spectrum and data obtained by performing the analysis on the second Z-spectrum.

7. A magnetic resonance imaging apparatus comprising:
   sequence controlling circuitry configured to execute a pulse sequence including application of a Magnetization Transfer (MT) pulse; and
   processing circuitry configured to generate an image by performing an analysis based on a Z-spectrum generated based on data obtained by executing the pulse sequence and configured to cause a display to display the generated image by dividing the image into a plurality of segments and using mutually-different dynamic ranges for the plurality of segments.

8. The magnetic resonance imaging apparatus according to claim 7, wherein the processing circuitry is configured to divide a region of Cerebrospinal Fluid (CSF) into the plurality of segments and causes the display to display the CSF by varying the dynamic range among the plurality of segments resulting from the division.

9. The magnetic resonance imaging apparatus according to claim 7, wherein the plurality of segments are segments that are radially divided while using a feature point as a center.

10. The magnetic resonance imaging apparatus according to claim 7, wherein the processing circuitry is further configured to:
perform the analysis to decompose the Z-spectrum into a sum of a plurality of spectra, and
generate the image based on at least one selected from between intensities and widths of the plurality of spectra.

11. An image processing method implemented by an image processing apparatus, the image processing method comprising:
generating an image by performing an analysis based on a Z-spectrum generated based on data obtained by executing a pulse sequence including application of a Magnetization Transfer (MT) pulse; and
causing a display to display the generated image by dividing the image into a plurality of segments and using mutually-different dynamic ranges for the plurality of segments.

12. The method according to claim 11, wherein a region of Cerebrospinal Fluid (CSF) is divided into the plurality of segments, and
wherein causing the display to display the generated image comprises causing the display to display the CSF by varying the dynamic range among the plurality of segments resulting from the division.

13. The method according to claim 11, wherein the plurality of segments are segments that are radially divided while using a feature point as a center.

14. The method according to claim 11, further comprising:
performing the analysis to decompose the Z-spectrum into a sum of a plurality of spectra, and
generating the image based on at least one selected from between intensities and widths of the plurality of spectra.

* * * * *